US008663674B2

(12) United States Patent
Wen et al.

(10) Patent No.: US 8,663,674 B2
(45) Date of Patent: Mar. 4, 2014

(54) MICROPARTICLE CONTAINING MATRICES FOR DRUG DELIVERY

(75) Inventors: Jie Wen, Eden Prairie, MN (US); Aron B. Anderson, Minnetonka, MN (US)

(73) Assignee: Surmodics, Inc., Eden Prairie, MN (US)

( * ) Notice: Subject to any disclaimer, the term of this patent is extended or adjusted under 35 U.S.C. 154(b) by 701 days.

(21) Appl. No.: 11/652,852

(22) Filed: Jan. 12, 2007

(65) Prior Publication Data

US 2007/0275027 A1    Nov. 29, 2007

Related U.S. Application Data

(60) Provisional application No. 60/759,241, filed on Jan. 13, 2006.

(51) Int. Cl.
*A61F 2/00* (2006.01)
*A61K 38/00* (2006.01)

(52) U.S. Cl.
USPC ............................................. 424/422; 514/2

(58) Field of Classification Search
None
See application file for complete search history.

(56) References Cited

U.S. PATENT DOCUMENTS

| | | | |
|---|---|---|---|
| 4,638,045 A | | 1/1987 | Kohn et al. |
| 5,645,593 A | | 7/1997 | Woods et al. |
| 5,660,854 A | | 8/1997 | Haynes et al. |
| 5,879,707 A | * | 3/1999 | Cartilier et al. ............... 424/468 |
| 5,879,713 A | | 3/1999 | Roth et al. |
| 6,143,037 A | | 11/2000 | Goldstein et al. |
| 6,228,393 B1 | | 5/2001 | DiCosmo et al. |
| 6,261,537 B1 | | 7/2001 | Klaveness et al. |
| 6,503,556 B2 | | 1/2003 | Harish et al. |
| 6,673,385 B1 | | 1/2004 | Ding et al. |
| 7,125,577 B2 | | 10/2006 | Chappa |
| 2002/0138154 A1 | | 9/2002 | Li et al. |
| 2002/0168394 A1 | | 11/2002 | Hossainy et al. |
| 2002/0188037 A1 | | 12/2002 | Chudzik et al. |
| 2003/0078647 A1 | | 4/2003 | Vallana et al. |
| 2003/0093107 A1 | | 5/2003 | Parsonage et al. |
| 2003/0129130 A1 | * | 7/2003 | Guire et al. .................. 424/1.11 |
| 2004/0023028 A1 | | 2/2004 | Yaszemski et al. |
| 2004/0033241 A1 | | 2/2004 | Donovan |
| 2004/0062875 A1 | | 4/2004 | Chappa et al. |
| 2004/0133155 A1 | | 7/2004 | Varner et al. |
| 2005/0019371 A1 | | 1/2005 | Anderson et al. |
| 2005/0095267 A1 | | 5/2005 | Campbell et al. |
| 2005/0119723 A1 | | 6/2005 | Peacock |
| 2005/0129130 A1 | * | 6/2005 | Shen et al. ............... 375/240.24 |
| 2005/0208095 A1 | | 9/2005 | Hunter et al. |
| 2005/0261283 A1 | | 11/2005 | Sukhatme |

FOREIGN PATENT DOCUMENTS

| | | |
|---|---|---|
| WO | WO93/06925 | 4/1993 |
| WO | WO01/89595 | 11/2001 |
| WO | WO2005/018606 | 3/2005 |
| WO | WO2005/099667 | 10/2005 |

OTHER PUBLICATIONS

Lee et al, Journal of Controlled release, 83, 437-452 (2002).*
Panyam, et al, Advanced Drug Delivery reviews, 55, 329-347 (2003).*
Merck Index (14th Edition—2nd Electronic Update, 2006, Merck & Co. Inc.).*
Gold Sodium Thiomalate MSDS in www.spectrum chemical.com/MSDS/ G3306.Pdf (accessed from the internet on Feb. 15, 2012).*
Acetaminophen in www.drugbank.ca/drugs /DB00316.*
International Search Report for corresponding International Patent Application No. PCT/US2007/000944, completed Aug. 23, 2007, 4 pgs.
Colombo, P., et al., Analysis of the swelling and release mechanisms from drug delivery systems with emphasis on drug solubility and water transport, J. Controlled Release, 39:231-237(1996).
Reza, M.S., et al., Comparative evaluation of plastic, hydrophobic and hydrophilic polymers as matrices for controlled-release drug delivery, J. Pharm. Pharmaceut. Sci. 6:274-291(2003).
Leach, K.J., et al., Degradation of double-walled polymer microspheres of PLLA and P(CPP:SA)20:80. II. In vivo degradation, Biomaterials, 19:1981-1988 (1998).
Lee, T.H., et al., Double-walled microspheres for the sustained release of a highly water soluble drug: characterization and irradiation studies, J. Controlled Release, 83:437-452 (2002).
Tan, E.C., et al., Fabrication of double-walled microspheres for the sustained release of doxorubicin, J. Colloid. Interface Sci., 291:135-143 (2005).
Pekarek, K.J., et al. Double-walled polymer microspheres for controlled drug release, Nature, 367:258-260 (1994).

* cited by examiner

*Primary Examiner* — Dennis Heyer
(74) *Attorney, Agent, or Firm* — Kagan Binder, PLLC

(57) ABSTRACT

Polymeric matrices including microparticles that provide sustained release of a hydrophilic bioactive agent are described. The matrices can be in the form of a coating on the surface of an implantable medical article or an in situ formed matrix. The microparticles of the matrix include a first polymer and a second polymer that modulates release of the hydrophilic bioactive agent from the matrix.

24 Claims, 2 Drawing Sheets

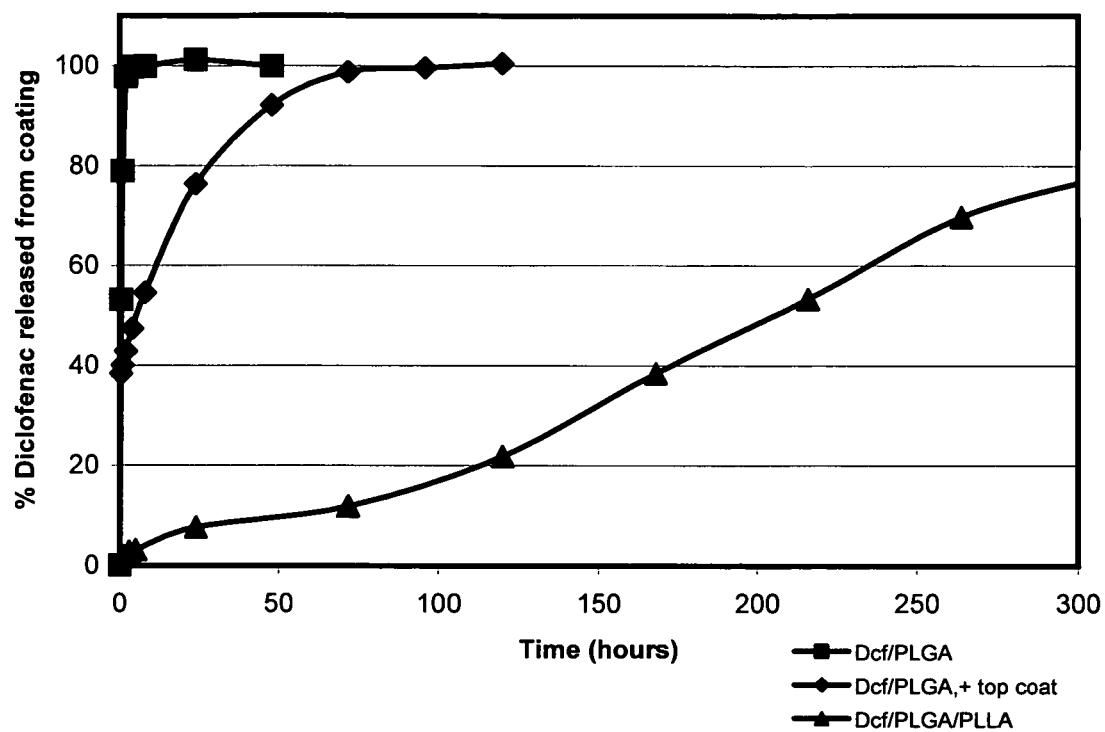

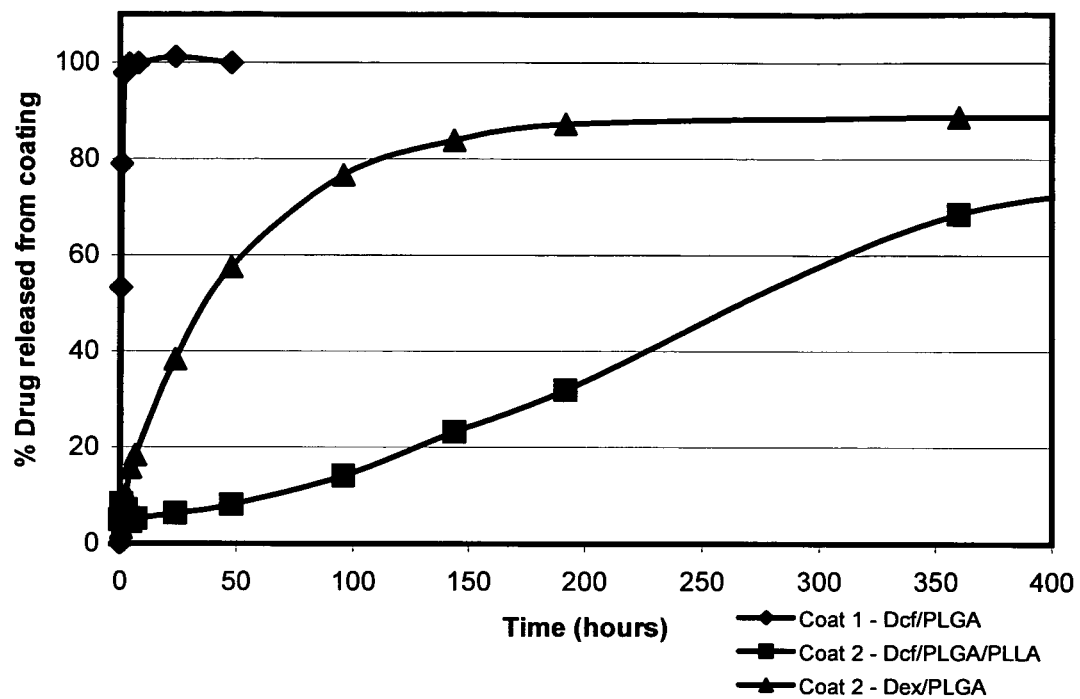

MICROPARTICLE CONTAINING MATRICES FOR DRUG DELIVERY

CROSS-REFERENCE TO RELATED APPLICATION

The present non-provisional patent Application claims priority under 35 USC §119(e) from United States Provisional Patent Application having Ser. No. 60/759,241, filed on Jan. 13, 2006, and titled MICROPARTICLE CONTAINING MATRICES FOR DRUG DELIVERY, wherein the entirety of said provisional patent application is incorporated herein by reference.

FIELD OF THE INVENTION

The present invention relates to the field of hydrophilic drug delivery from implanted polymeric matrices.

BACKGROUND OF THE INVENTION

Implantable medical devices having thin polymeric coatings containing therapeutic compounds that are released from the coating to provide a local therapeutic effect in the vicinity of the coated device have been shown to be valuable for the treatment of various medical conditions, in particular those conditions involving diseases of the cardiovascular system. For example, delivery of a therapeutic agent from the device surface can prevent cellular responses initiated by the presence of the implantable device. The therapeutic agent that is released from the coating can prevent conditions that would otherwise shorten the functional life of the device following implantation. Therapeutic agents released from the coating may also be directed at treating a diseased area of the body.

For example, stents having a coating containing a therapeutic agent can provide localized release of a therapeutic substance at the site of administration. Local administration of therapeutic agents via polymeric coatings on stents has shown favorable results in reducing restenosis. Several classes of drug-polymer chemistries have been explored for use in stent coatings as found in current art, some of which have been approved and are currently being used in medical procedures. Many of these chemistries are useful for delivering hydrophobic therapeutic agents.

For example, coating compositions based on poly(alkyl (meth)acrylate) and poly(ethylene-co-vinyl acetate) mixtures suitable for preparing coatings for hydrophobic drug (such as rapamycin) release are described in U.S. Pat. No. 6,214,901. Release of hydrophobic bioactive agents in a controlled manner can be achieved using this type of polymeric coating system. For example, sustained and controlled release of the hydrophobic drug, wherein less than 50% of the total quantity of the hydrophilic drug released is released in the first 24 hours.

Another hydrophobic polymer system stated to be useful for drug delivery is described in U.S. Pat. No. 6,669,980, which teaches preparation of medical devices having coatings that include poly(styrene-isobutylene-styrene).

Yet other hydrophobic polymer systems useful for drug delivery are described in U.S. Patent Publication Nos. 2005/0220843 and 2005/0244459.

In addition to the desirable drug-release profiles, many of the coatings that are formed using hydrophobic polymeric systems are durable and compliant. These properties are desirable as the surface of the device typically encounters frictional forces. A durable and compliant coating will generally not be damaged if the coated device is subject to bending or manipulation, which often occurs with stents. These properties prevent the coating from delaminating or cracking during use.

In addition, coatings formed from hydrophobic polymeric systems can be relatively thin, which is also a desirable property when the coating is formed on medical devices having complex geometries. Compositions and methods that allow the formation of thin coatings of polymeric material on the device surface can prevent formation of webs of polymeric material between features of the device.

While these references appear to have demonstrated suitable coating systems for hydrophobic drug release, systems for hydrophilic drug release are not as well developed. Coatings designed to release a hydrophilic bioactive agent have been problematic because release is typically inadequately controlled. These coatings may also the lack desirable physical properties, such as durability.

In many cases, the majority of the hydrophilic bioactive agent is released from the coating in a short burst, resulting in depletion of the bioactive agent from the coating. This burst is particularly undesirable when a therapeutic effect is required over an extended period of time. This short term burst is thought to be caused by the hydrophilicity of the bioactive agent driving water into the polymeric coating, causing an increase in the osmotic pressure in the coating. As a result, the permeability of the coating for the hydrophilic drug is significantly increased, resulting in the elution of the drug at a therapeutically ineffective rate. This effect can happen in coatings having both smaller and larger hydrophilic molecules Controlling the permeability of water into the polymer coating by reducing the hydrophilicity of the coating, for example, by using a hydrophobic polymer, can provide one way of minimizing water absorption and the inadequate release of the hydrophilic bioactive agent. As indicated, hydrophobic polymers are preferred for the benefits of durability and conformity.

However, the hydrophobic polymer may be incompatible with solvent systems that are required to dissolve the hydrophilic drug. The hydrophilic drug may rapidly phase separate in an uncontrolled manner resulting in drug aggregation in the coating. This system can therefore produce coatings with unpredictable and variable release rate profiles. This situation is undesirable, as coatings displaying reproducible release rates cannot be formed. Furthermore, particles of hydrophilic drug also weaken a hydrophobic coating and cause local areas of high swelling.

Preparing coatings having hydrophilic properties is also challenging from the standpoint of designing hydrophilic bioactive agent-releasing coatings. Coatings that are highly hydrophilic can rapidly absorb water and cause plasticization of the polymer, resulting in a soft gel-like coating. This characteristic is also undesirable as the polymer can tear upon expansion, resulting in partial or full destruction of the coating. Furthermore, excessive water swelling not only weakens the polymer, but may increase the diffusivity of the drug, resulting in loss of release control.

SUMMARY OF THE INVENTION

The invention generally relates to polymeric matrices that contain microparticles containing a bioactive agent, wherein the matrices are capable of releasing the bioactive agent when placed in contact with body tissue or fluid. The matrix can be in the form of a coating formed on the surface of an implantable medical device, or can be independent of a device, such as a matrix that is formed in situ containing microparticles.

The matrix includes at least one set of microparticles. The microparticles comprise a hydrophilic bioactive agent, a first polymer, and a second polymer. In conjunction with the polymeric matrix, which allows fluid to penetrate the matrix and contact the microparticles, the second polymer of the microparticle modulates the release of the bioactive agent from the matrix. For example, the second polymer can reduce the rate of release of the bioactive agent from the matrix relative to the rate of release of the bioactive agent from a matrix having microparticles that do not include the second polymer.

The matrices can be fabricated so the hydrophilic bioactive agent is released from the matrix with a sustained-release profile. These matrices can avoid a short-term burst of hydrophilic bioactive agent and premature depletion of the hydrophilic bioactive agent from the matrix. This represents a distinct improvement over hydrophilic bioactive agent-containing systems previously described. The sustained-release profiles of the microparticle-containing matrices of the present invention allow for release of the hydrophilic bioactive agent from an implantable medical device over a longer and more therapeutically useful time period.

The matrix can be used for the sustained-release delivery of bioactive agents that have a solubility of greater than 1 part bioactive agent per 50 parts water. For example the microparticles can include a hydrophilic bioactive agent that is soluble, freely soluble, or very soluble in water. In some aspects the hydrophilic bioactive agent is an ionizable molecule. In some cases the ionizable molecule in an un-ionized form is substantially less soluble than in an ionized form.

In some aspects, the first and second polymers of the microparticle are degradable polymers. In order to reduce the rate of release of bioactive agent from the matrix, the microparticles can comprise a second biodegradable polymer that has a rate of degradation that is slower than the first biodegradable polymer. In some cases, the second biodegradable polymer is a biodegradable homopolymer and the first biodegradable polymer is a biodegradable copolymer. Exemplary first and second polymers are synthetic degradable polymers, such as PLLA and PLGA.

In some aspects, the microparticles can be structured so that a predominant amount of second polymer is in mixture with the bioactive agent. For example, the microparticles can include a core-shell structure, wherein the core comprises the first polymer in mixture with the bioactive agent, and the shell comprises the second polymer.

In some aspects the matrix comprises polymer and reacted groups. The reacted groups can covalently couple the polymeric material together, or covalently couple the polymeric material to a surface of a device in the case of a coating, or both.

In some aspects, the matrix is formed of hydrophilic polymers. Exemplary polymers include poly(vinylpyrrolidone) and poly(acrylamide). In some cases, the reacted groups of the matrix are photoreactive groups that have been activated to bond the polymer to a device surface and/or another polymer. In some cases, the reacted groups are latent reactive groups that have been activated and that are pendent from the polymer. The matrix can also comprise a biodegradable polymer; however, it is preferred that the primary polymer component of the matrix is either non-biodegradable, or less biodegradable than the microparticle polymer, if degradable polymers are used.

In some aspects, the microparticles have a size of less than 50 μm. In some aspects, the matrix is in the form of a coating on an implantable medical device. The coating includes microparticles immobilized in the matrix, the microparticle comprising a water-soluble bioactive agent, a first polymer, and a second polymer, wherein the second polymer modulates release of the bioactive agent from the coating. Exemplary implantable medical devices are intravascular and intraocular medical devices. In some aspects, the coating is formed of a matrix of polymeric material comprising reacted groups (which form the coating) and microparticles immobilized in the polymeric matrix. The coating has properties that are suitable for use within a patient.

This microparticle composition, in conjunction with the polymeric matrix, provides a particularly effective mechanism for the sustained delivery of not only smaller hydrophilic bioactive agents, but also larger hydrophilic bioactive agents. For example, the present matrix can also be used to deliver large hydrophilic bioactive agents, such as polypeptides, polysaccharides, or polynucleotides, from the surface of the device.

Therefore, in some aspects, the microparticles immobilized in the matrix comprise a hydrophilic bioactive agent having a molecular weight of 1,000 Da or greater. In some aspects, the device has a bioactive agent release profile wherein not more than 50% of the bioactive agent present in the coating is released within a period of 24 hours. In more specific aspects, the device has a bioactive agent release profile wherein not more than 50% of the bioactive agent present in the coating is released within a period of 1 to 29 days, 2 to 18 days, 3 to 11 days, or 4 to 8 days.

The invention also provides a method for forming a matrix, which releases bioactive agent at a target location in the body where it is implanted or formed in situ. The method comprises a step of providing a composition comprising (a) a polymeric material and latent reactive groups and (b) at least one set of microparticles, the microparticles comprising a water soluble bioactive agent, a first polymer, and a second polymer, wherein the second polymer modulates release of the bioactive agent from the matrix. The composition is then treated to provide a matrix comprising immobilized microparticles. In some cases the composition is provided to a surface of an implantable medical device.

The step of treating can result in bonding the matrix polymers to each other, the surface of a device, or both, thereby forming the polymeric matrix having immobilized microparticles.

The invention also provides a method for localized, sustained release delivery of a hydrophilic bioactive agent to a subject. The method comprises a step of placing or forming in a subject a matrix comprising the hydrophilic bioactive agent-containing microspheres immobilized in a matrix of polymeric material. The hydrophilic bioactive agent is released from the matrix to provide a therapeutic benefit to the patient over an extended period of time. In some aspects the hydrophilic bioactive agent is released from a coating on the surface of a medical device.

The matrix can optionally include one or more sets of other microparticles (e.g., a second set) that include a bioactive agent that is different than the hydrophilic bioactive agent. For example, the matrix of the present invention can also be used to concurrently deliver a second bioactive agent that is less soluble in water than the first hydrophilic bioactive agent. The second bioactive agent can be a hydrophobic bioactive agent that has little or no solubility in water. From this standpoint, the matrix is particularly advantageous as two types of bioactive agents having different solubility characteristics can be delivered from the same matrix, both bioactive agents being released in a sustained manner, and generally within their respective therapeutic windows. This arrangement can provide many benefits to a patient, particularly when the presence of the two bioactive agents results in an improvement over administration of one bioactive agent, such as might be observed with an additive or synergistic effect.

Therefore, in another aspect, the invention provides a matrix which releases at least two bioactive agents at a target location in the body where the matrix is implanted or formed in situ. The matrix is formed of a polymeric material that allows fluid to penetrate the matrix, and the matrix comprises a first set of microparticles immobilized in the matrix. The microparticles of the first set comprise a water-soluble bioactive agent, a first polymer, and a second polymer, and the second polymer delays release of the bioactive agent from the matrix. The matrix also comprises a second set of microparticles immobilized in the matrix, the microparticles of the second set comprising a bioactive agent that is different than the water-soluble bioactive agent. In some aspects the matrix is in the form of a coating on the surface of an implantable medical device.

In some aspects, the matrix has a release profile wherein the first and second bioactive agents are released from the matrix at rates wherein not more than 50% of either the first or second bioactive agent is released from the matrix within a period of 24 hours.

In more specific aspects, 25% of the first bioactive agent and 50% of the second bioactive agent present in the matrix are released at time points within a period of 4.7 hours to 8 days.

In other specific aspects, the first bioactive agent is soluble in water and the second bioactive agent is practically insoluble or insoluble in water. In yet other specific aspects, the first and second bioactive agents have molecular weights of 400 Da or less.

The invention also provides a coating having specific hydrophilic bioactive agent release profiles. Accordingly, in yet other aspects, the invention provides a medical device having a bioactive agent-releasing coating having a bioactive agent release profile wherein 50% of the bioactive agent present in the coating is released within a period of 1 to 27 days. The release of bioactive agent can be determined by the methods as discussed herein. In more specific cases, the 50% of the hydrophilic bioactive agent present in the coating is released within a period of 3 to 15 days, 5 to 13 days, or 7 to 111 days.

BRIEF DESCRIPTION OF THE DRAWINGS

FIG. 1 is a graph representing release of diclofenac from (a) a hydrophilic polymeric coating containing diclofenac/PLGA microparticles, (b) a hydrophilic polymeric coating containing diclofenac/PLGA microparticles with additional polymer topcoat, and (c) a hydrophilic polymeric coating containing diclofenac/PLGA/PLLA microparticles.

FIG. 2 is a graph representing release of diclofenac from (a) a hydrophilic polymeric coating containing diclofenac/PLGA microparticles, and the release of diclofenac and dexamethasone from (b) a hydrophilic polymeric coating containing diclofenac/PLGA/PLLA microparticles and dexamethasone/PLGA microparticles.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Generally, the present invention provides methods for the delivery of a hydrophilic bioactive agent from a polymeric matrix, wherein the matrix includes a plurality of immobilized microparticles, the microparticles including the hydrophilic bioactive agent. In some cases, the matrix includes reacted groups, which allows the polymeric material to be covalently bonded to another moiety, such as a surface of a device, or to another polymer present in the matrix.

In some aspects, the microparticles are immobilized in a matrix that is part or all of a coating on the surface of an implantable medical device. In other aspects the microparticles are immobilized in a matrix that is not necessarily associated with a medical device. For example, the microparticles can be immobilized in a mass (matrix) of polymeric material, the polymers being bonded together by reactive groups between the polymers. In this case the matrix may be formed in situ, such as on a tissue at a desired location in the body.

To facilitate discussion of the invention, reference to a "matrix" is intended to include matrices in the form of coatings, such as those on implantable medical devices, as well as matrices formed in situ, such as on a tissue.

The term "immobilized" refers to the microparticles being relatively stationary in the matrix and not released when the polymeric matrix is intact. A matrix with immobilized microparticles is advantageous from the standpoint that at least most of the bioactive agent, and more typically substantially all of the bioactive agent that is released, is released from the matrix. In this regard, the matrix is very useful for providing a localized therapeutic effect in the vicinity of, for example, an implanted article or an in-situ formed matrix.

In many aspects, the microparticles can be immobilized in the coating by providing a polymeric matrix that has an average pore size that is smaller than the diameter of the microparticles. In such an arrangement, the microparticles are hindered from being removed from the coating or matrix by fluid movement.

With regard to bioactive agent release, immobilization of bioactive agent-releasing microparticles in the matrix is generally beneficial as it promotes a localized therapeutic effect. By comparison, microparticles that are released from a matrix may not provide effective localized therapy. For example, if a substantial amount of microparticles is otherwise released, the microparticles may travel to and be sequestered at a location of the body other than the desired site, resulting in a mistargeted release of the bioactive agent.

If there are differences in the overall stability between the matrix and the microparticles, generally, and preferably, the matrix is more stable than the microparticles. For example, in some aspects, the matrix includes a biostable polymer and the microparticles include a biodegradable polymer. However, in other aspects, both the matrix and microparticles can include biodegradable polymers. In these aspects, the microparticles preferably degrade faster than the polymeric matrix. If degradation of both the microparticles and matrix occur upon contact with body fluid, the microparticles will degrade at a faster rate than that of the matrix, and loss of the microparticles from the surface of the device can be prevented.

The microparticles can be of any size and shape that is sufficient to be immobilized in the matrix. In some cases, wherein it is desired to use very small microparticles, and wherein it is desired to keep the microparticles immobilized in the matrix, matrix formation can be enhanced, for example, by increasing bonding between the polymers of the matrix. This feature can effectively reduce the pore size within the matrix.

Depending on the application, it can be desirable to use microparticles within a particular size range. For example, for a coating on the surface of a medical device, it is generally desirable to utilize a microparticle that has a diameter that is smaller than the thickness of the coating. In many aspects, a coating is prepared using microparticles that are less than 50 µm in diameter. However, for matrices that are formed in situ, the microparticle diameter can be greater or less than 50 µm.

Microparticles can be used that are very small, such as in the nanometer range. However, in some modes of practice, microparticles that have a diameter of 100 nm or larger, and more desirably 400 nm or larger, can be used in the preparation of hydrophilic bioactive agent-releasing matrices. U.S. Patent Pub No. 2003/0129130 demonstrates that matrices formed from a polymer having pendent photoreactive groups retained 400 nm diameter microparticles, without bonding the microparticles to the polymeric material. However, the matrix may be formed from the polymerization of polymers (macromers) having a high density of polymerizable groups, thereby forming a highly crosslinked network of polymers capable of immobilizing microparticles in the nanometer range.

To illustrate aspects of the invention, a coating that provides hydrophilic bioactive agent with a sustained-release profile can be prepared utilizing microparticles comprising a hydrophilic bioactive agent, a first polymer, and a second polymer. In conjunction with the polymeric matrix, which allows fluid to penetrate the matrix and contact the microparticles, the second polymer of the microparticle modulates the release of the bioactive agent from the coating. In particular, the second polymer can reduce the rate of release of the bioactive agent from the matrix. The reduction in rate of release is compared to the rate of release of the bioactive agent from a matrix having microparticles wherein the second polymer is not included in the microparticles.

In these aspects, the microparticle includes at least two polymers (the first and second polymers); additional polymers may optionally be included in the microparticles. For example, the microparticles can include a third, fourth, fifth polymer, etc. At least one of the two polymers in the microparticle modulates release of the bioactive agent from the microparticle, thereby modulates release of the bioactive agent from the matrix.

The choice of the polymer components in the microparticle can be chosen based on the present disclosure, as well as knowledge available to one of skill in the art. In some aspects, a suitable second polymer, when associated with the microparticle, will modulate release by reducing the rate of release of the bioactive agent from the matrix as compared to a matrix having a microparticle that does not include the second polymer.

Selection of a second polymer to provide such an effect can be illustrated by the following method. First, microparticles are obtained or prepared formed of a first polymer material and including a hydrophilic bioactive agent. The microparticles are immobilized in a polymeric matrix, as described herein, and the rate of release of the hydrophilic bioactive agent is tested. Next, microparticles are obtained or prepared formed of the first polymer, the bioactive agent, a second selected polymer, which is the variable factor. These microparticles are immobilized in a polymeric matrix and the rate of release of the hydrophilic bioactive agent is tested to determine if the second polymer modulates release of the bioactive agent. The second polymer can be selected to reduce the rate of release of the hydrophilic bioactive agent as compared to microparticles that do not include the second polymer.

This phenomenon is exemplified by comparison of the data in Tables 3 and 1, which show that release of the water-soluble bioactive agent diclofenac from PVP matrices having PLGA/PLLA/diclofenac microparticles is substantially delayed in comparison to PVP matrices having PLGA/diclofenac microparticles (about a 97% reduction in release rate as measured at one hour).

Surprisingly, the inclusion of a polymer topcoat on the PVP matrices having PLGA/diclofenac microparticles (see Example 2 and Table 2; as compared to the second polymer being included with the microparticles) only moderately reduced the rate of release of diclofenac (about a 49% reduction in release rate as measured at one hour).

The first and second polymers can be selected from the group of synthetic and natural polymers. The synthetic and natural polymers can be biostable or biodegradable.

In some aspects the microparticle can include a non-biodegradable polymer. Exemplary non-biodegradable polymers include, for example, synthetic polymers such as poly (methylmethacrylate), polystyrene, polyethylene, polypropylene, polyamide, polyester, polyinylidenedifluoride (PVDF), and the like.

In some cases, selection of a first and second biostable polymer can be performed based on known or calculated glass transition temperatures ($T_g$) of selected polymers. $T_g$ is the specific temperature at which a polymer transitions from a glassy state to a rubbery state. $T_g$ is an inherent, physical property of polymers that can be obtained from the technical literature (for example, see Thermal Analysis of Polymeric Materials Wunderlich, B. (2005) Springer, Berlin; or Handbook of Polymer Synthesis, Kricheldorf et al. (2005) Marcel Dekker, New York) or determined using analytical techniques such as differential scanning calorimetry (DSC), or by mathematical techniques such as the Fox equation Fox, T. G. (1956) *Bull. Am. Physics Soc.* 1, 3, p. 123.

In one mode of practice, the microparticle comprises a first polymer that has a lower Tg than a second polymer. The second polymer, which is harder, can reduce the rate of release of the bioactive agent from the matrix. For example, the Tg of a suitable first polymer such as PLGA is about 45° C., and the Tg of a suitable second polymer such as PLLA is about 55° C.

In some aspects the difference between the Tg of the first and second polymer is about 5° C. or greater. In more specific aspects the difference between the Tg of the first and second polymer is about 10° C. or greater.

In some aspects, the first and second polymers have Tgs of about 35° C. or greater. In more specific aspects the first and second polymers have Tgs in the range of about 35° C. to about 65° C.

Selection of the first and second polymers can also be based on other properties of the polymers such as molecular weight, solubility, and rheology.

In some aspects and in exemplary modes of practice, the microparticle is fabricated from biodegradable polymers. As used herein, biodegradable polymers are capable of being broken down by various enzymes, such as those in the normal functioning of the human body and living organisms (such as bacteria) and/or in water environments (by simple hydrolysis). Once broken down, the degradation products of these polymers are gradually absorbed or eliminated by the body.

Natural or synthetic biodegradable polymers can be used. In one preferred mode of practice, the microparticles include two or more synthetic biodegradable polymers, one of which delays release of the bioactive agent from the microparticle.

In some cases, selection of a first and second biodegradable polymer can be performed based on known or calculated rates of degradation of selected polymers. In one mode of practice, the microparticle comprises a first biodegradable polymer that has a faster rate of degradation than a second polymer. The second polymer, which is more slowly degrading, reduces the rate of release of the bioactive agent from the matrix.

One way of measuring the rates of degradation of first and second biodegradable polymers involves obtaining or preparing microparticles formed of a particular polymer, and then determining the rate of degradation of the microparticles in a liquid environment. In some cases the liquid environment can include body fluid taken from a part of the body where the matrix will be formed or implanted. For example, the body fluid can include blood serum or vitreal fluid from the eye. A second polymer from a microparticle that displays a slower rate of degradation can be used in combination with a first polymer from a microparticle that displays a faster rate of degradation.

In some cases, the first polymer is a biodegradable copolymer (referring to polymers formed from two or more types of polymeric units) and second polymer is a biodegradable homopolymer. The (first) biodegradable copolymer may form an amorphous polymeric domain that is more susceptible to degradation than a (second) biodegradable homopolymer that may form a semi-crystalline or crystalline polymeric domain.

In some modes of practice, the first and/or second synthetic biodegradable polymer is selected from the group of polyesters such as poly(lactic acid) (poly(lactide)), poly(glycolic acid) (poly(glycolide)) poly(lactide-co-glycolide), poly(dioxanone); polylactones such as poly(caprolactone) and poly (valerolactone), copolymers such as poly(glycolide-co-polydioxanone), poly(glycolide-co-trimethylene carbonate), and poly(glycolide-co-caprolactone); poly(3-hydroxybutyrate), poly(3-hydroxyvalerate), poly(tartronic acid), poly(β-malonic acid), poly(propylene fumarate); degradable polyesteramides; degradable polyanhydrides and polyalkeneanhydrides (such as poly(sebacic acid), poly(1,6-bis(carboxyphenoxy) hexane, poly(1,3-bis(carboxyphenoxy)propane); degradable polycarbonates and aliphatic carbonates; degradable polyiminocarbonates; degradable polyarylates; degradable polyorthoesters; degradable polyurethanes; degradable polyphosphazenes; degradable polyhydroxyalkanoates; degradable polyamides; degradable polypeptides; and copolymers thereof. In some aspects, two or more synthetic biodegradable polymers selected from these polymers are used to fabricate the microparticle including the bioactive agent, one of which delays release of the bioactive agent from the matrix.

Some biodegradable poly(ester-amides) are described in U.S. Pat. No. 6,703,040. These poly(ester-amides) can be formed by the polymerization of a diol (D), a dicarboxylic acid (C) and an alpha-amino acid (A) through ester and amide links in the form $(DACA)_n$.

Biodegradable polyetherester copolymers can also be used. Generally speaking, the polyetherester copolymers are amphiphilic block copolymers that include hydrophilic (for example, a polyalkylene glycol, such as polyethylene glycol (PEG)) and hydrophobic blocks (for example, polyethylene terephthalate). Examples of block copolymers include poly (ethylene glycol)-based and poly(butylene terephthalate)-based blocks (PEG/PBT polymer). Examples of these types of multiblock copolymers are described in, for example, U.S. Pat. No. 5,980,948. PEG/PBT polymers are commercially available from Octoplus BV (Leiden, Netherlands), under the trade designation PolyActive™.

Other PEG-containing block copolymers, such as those including one or more polymeric blocks selected from poly (hydroxybutyrate) (PHB), poly(oxyethylene) (POE), poly (caprolactone) (PCL), and poly(lactide) (PLA) are available from Advanced Polymer Materials, Inc. (Lachine, QC, Canada).

Biodegradable copolymers having a biodegradable, segmented molecular architecture that includes at least two different ester linkages can also be used. The biodegradable polymers can be block copolymers (of the AB or ABA type) or segmented (also known as multiblock or random-block) copolymers of the $(AB)_n$ type. These copolymers are formed in a two (or more) stage ring opening copolymerization using two (or more) cyclic ester monomers that form linkages in the copolymer with greatly different susceptibilities to transesterification. Examples of these polymers are described in, for example, U.S. Pat. No. 5,252,701 (Jarrett et al., "Segmented Absorbable Copolymer").

Other exemplary multi-block copolymers have a structure according to any of the formulae (1)-(3) as described in EP 1555278:

$$[—R_1\text{-Q1-}R_4\text{-Q2-}]_x\text{-}[R_2\text{-Q3-}R_4\text{-Q4-}]_y\text{-}[R_3\text{-Q5-P4-Q6-}]_z\text{-} \quad (1)$$

$$[—R_1—R_2—R_1\text{-Q1-}R_4\text{-Q2-}]_x\text{-}[R_3\text{-Q2-}R_4\text{-Q1}]_z\text{-} \quad (2)$$

$$[—R_2—R_1—R_2\text{-Q1-}R_4\text{-Q2-}]_x\text{-}[R_3\text{-Q2-}R_4\text{-Q1}]_z\text{B—} \quad (3)$$

$R_1$ and $R_2$ may be amorphous polyester, amorphous polyetherester or amorphous polycarbonate; or an amorphous pre-polymer that is obtained from combined ester, ether and/or carbonate groups. $R_1$ and $R_2$ may contain polyether groups, which may result from the use of these compounds as a polymerization initiator, the polyether being amorphous or crystalline at room temperature. However, the polyether thus introduced will become amorphous at physiological conditions. $R_1$ and $R_2$ are derived from amorphous pre-polymers or blocks A and B, respectively, and $R_1$ and $R_2$ are not the same. $R_1$ and $R_2$ may contain a polyether group at the same time, but it is preferred that only one of them contains a polyether group. "z" is zero or a positive integer. $R_3$ is a polyether, such as poly(ethylene glycol), and may be present ($z \neq 0$) or not ($z=0$). $R_3$ will become amorphous under physiological conditions. $R_4$ is an aliphatic $C_2$-$C_8$ alkylene group, optionally substituted by a $C_1$-$C_{10}$ alkylene, the aliphatic group being linear or cyclic, wherein $R_4$ is preferably a butylene, $—(CH_2)_4$-group, and the $C_1$-$C_{10}$ alkylene side group may contain protected S, N, P or O moieties. "x" and "y" are both positive integers, which are both preferably at least 1, whereas the sum of "x" and "y" (x+y) is preferably at most 2000, more preferably at most 500, most preferably at most 200. Q1-Q6 are linking units obtained by the reaction of the pre-polymers with the multifunctional chain-extender. Q1-Q6 are independently amine, urethane, amide, carbonate, ester or anhydride. The event wherein all linking groups Q are different being rare and is not preferred.

Other suitable biodegradable polymer materials include biodegradable terephthalate copolymers that include a phosphorus-containing linkage. Polymers having phosphoester linkages, called poly(phosphates), poly(phosphonates) and poly(phosphites), are known. See, for example, Penczek et al., Handbook of Polymer Synthesis, Chapter 17: "Phosphorus-Containing Polymers," 1077-1132 (Hans R. Kricheldorf ed., 1992), as well as U.S. Pat. Nos. 6,153,212, 6,485,737, 6,322,797, 6,600,010, 6,419,709. Biodegradable terephthalate polyesters can also be used that include a phosphoester linkage that is a phosphite. Suitable terephthalate polyester-polyphosphite copolymers are described, for example, in U.S. Pat. No. 6,419,709 (Mao et al., "Biodegradable Terephthalate Polyester-Poly(Phosphite) Compositions, Articles, and Methods of Using the Same). Biodegradable terephthalate polyester can also be used that include a phosphoester linkage that is a phosphonate. Suitable terephthalate polyester-poly(phosphonate) copolymers are described, for example, in U.S. Pat. Nos. 6,485,737 and 6,153,212 (Mao et al., "Biodegradable Terephthalate Polyester-Poly(Phosphonate) Compositions, Articles and Methods of Using the Same). Biodegradable terephthalate polyesters can be used that include a phosphoester linkage that is a phosphate. Suitable terephthalate polyester-poly(phosphate) copolymers are described, for example, in U.S. Pat. Nos. 6,322,797 and 6,600,010 (Mao et al., "Biodegradable Terephthalate Polyester-Poly(Phosphate) Polymers, Compositions, Articles, and Methods for Making and Using the Same).

Biodegradable polyhydric alcohol esters can also be used (See U.S. Pat. No. 6,592,895). This patent describes biodegradable star-shaped polymers that are made by esterifying polyhydric alcohols to provide acyl moieties originating from aliphatic homopolymer or copolymer polyesters. The biodegradable polymer can be a three-dimensional crosslinked polymer network containing hydrophobic and hydrophilic components that form a hydrogel with a crosslinked polymer structure, such as that described in U.S. Pat. No. 6,583,219. The hydrophobic component is a hydrophobic macromer with unsaturated group terminated ends, and the hydrophilic polymer is a polysaccharide containing hydroxy groups that are reacted with unsaturated group introducing compounds. In yet further embodiments, the biodegradable polymer can comprise a polymer based upon α-amino acids (such as elastomeric copolyester amides or copolyester urethanes, as described in U.S. Pat. No. 6,503,538).

Degradable polymers of the invention can also include dextran based polymers such as those described in U.S. Pat. No. 6,303,148. Exemplary dextran based degradable polymers including those available commercially under the tradename OCTODEX™.

Other biodegradable polymers include polymethylidenemalonate, polyhydroxybutyrate, and the like.

The microparticles can also be formed using natural biodegradable polysaccharides. Natural biodegradable polysaccharides having pendent coupling groups, such as polymerizable groups, can be reacted to form a body member with a cross-linked matrix of polysaccharides. Desirably, the natural biodegradable polysaccharides are low molecular weight polymers, such as having a molecular weight of about 50,000 Da or less, 25,000 Da or less, or 10,000 Da or less.

Natural biodegradable polysaccharides with pendent coupling groups are described in U.S. Pub. No. 2005/0255142, published Nov. 17, 2005, (Chudzik et al.) and U.S. patent application Ser. No. 11/271,213, filed Nov. 11, 2005 (Chudzik et al.), both commonly assigned to the applicant of the present invention. One preferred class of natural biodegradable polysaccharides are selected from the group of maltodextrin, amylose, and polyalditol.

The microparticles can also be formed using polysaccharides derivatized with hydrophobic moieties. Exemplary hydrophobic polysaccharides can be prepared according to methods described in U.S. Patent Application No. 60/782,957 (Chudzik, S. J.), filed Mar. 15, 2006, now Publication No. US2007/0260054A1, and assigned to the applicant of the present invention. The body member can be formed using a hydrophobic moiety derivatized with hydrophobic moieties comprising a $C_2$-$C_{18}$, linear, branched, or cyclic alkyl group, or a $C_2$-$C_{10}$, or a $C_2$-$C_6$, linear, branched, or cyclic alkyl group. In some aspects, the hydrophobic derivative of a natural biodegradable polysaccharide has a degree of substitution of greater than 1.

As an example, a bioactive agent containing biodegradable microparticle may be prepared with first and second hydrophobic polysaccharides, wherein the first hydrophobic polysaccharide has a Tg that is lower than the second hydrophobic polysaccharide. In some specific aspects, the first and second hydrophobic polysaccharides have Tgs of about 35° C. or greater, such as in the range of about 40° C. to about 65° C.

Other degradable polymers useful for the current invention can be obtained from, for example, Birmingham Polymers, Inc. (Birmingham, Ala. 35211). Degradable polymers and their synthesis have also been described in various references including Mayer, J. M., and Kaplan, D. L. ((1994) Trends in Polymer Science 2: pages 227-235; and Jagur-Grodzinski, J., (1999) Reactive and Functional Polymers: Biomedical Application of Functional Polymers, Vol. 39, pages 99-138. In some cases, the degradable polymer is degraded by the action of various enzymes in the body.

Degradable microparticles can be prepared incorporating various biologically active agents by established techniques, for example, the solvent evaporation technique (see, for example, Wiehert, B. and Rohdewald, P. J. Microencapsul. (1993) 10:195). The hydrophilic bioactive agent can be released from the microparticle, which is immobilized in the polymeric matrix on a substrate, upon degradation of the microparticle in vivo.

In some aspects of the invention, the microparticles are fabricated from a synthetic biodegradable homopolymer and a synthetic biodegradable co-polymer. For example, the microparticle can include polylactide and poly(lactide-co-glycolide).

In another desired mode of practice, the microparticle includes a bioactive agent, a first polymer, and a second polymer that controls the release of the bioactive agent, wherein the microparticle has a structure that comprises an inner portion composed primarily of the bioactive agent and the first polymer, and an outer portion composed primarily of the second polymer. More desirably, the first and second polymers are selected from synthetic biodegradable polymers.

In some cases, these types of microparticles are referred to as "double walled" microparticles (see, for example, Pekarek, K. J. (1994) Nature 367:258-60). However, the structure of a "double walled" microparticles is more accurately described as having a core including of one biodegradable polymer and a shell (or more than one shell) including another biodegradable polymer.

The inner portion (e.g., core) of the microparticle includes at least most of, if not all, of the bioactive agent present in the microparticle. Various techniques can be used to prepare microparticles having inner and outer portions. Some techniques are based on phase separation of a polymer mixture. Many phase separation techniques also involve solvent evaporation.

Microparticles comprising an inner portion and an outer portion can be prepared by first preparing a first composition that includes the first polymer and the bioactive agent. The first composition can be treated to provide a homogenous suspension of the first polymer and the bioactive agent. The homogenized first composition can then be combined with a second composition that includes the second polymer. The mixture of the first and second compositions can then be homogenized. After these steps microparticles can be formed by combining the composition with a solution that promotes formation of the microparticle, such as a polyvinylalcohol-containing solution. In one mode of practice, the microparticles can then be recovered by, for example, centrifugation, and then optionally washed, and frozen or lyophilized.

This method can be used for the preparation of microparticles that include a hydrophilic bioactive agent. To exemplify this process, a hydrophilic bioactive agent is combined with a first biodegradable polymer, such as PLGA, in a solvent, such as dichloromethane, to prepare the first composition. Just as one example, the concentrations of the hydrophilic bioactive agent and the first polymer can be about 62.5 mg/ml and 187.5 mg/ml, respectively. However depending on various factors, such as the properties of bioactive agent and the desired loading of the bioactive agent in the microparticle, the concentration of the hydrophilic bioactive agent and the first polymer can be appropriately chosen. A second composition is prepared having a second biodegradable polymer. The reagents in the first and second compositions are left for a period of time sufficient to dissolve the reagents, such as overnight. Following this step, the first composition can be homogenized, for example, by sonication, and then the second composition can be combined with the first composition. The mixture can then be homogenized again. After this microparticles can be combined with a solution, such as about a four-fold excess, of 1.0% (w/v) aqueous polyvinyl alcohol (PVA) solution and then vortexed. Following this step, the mixture can then be added to a larger volume (e.g., 20-fold excess) of a polyvinyl alcohol (PVA) solution (e.g., 0.5% PVA). In one mode of practice, the microparticles can then be recovered by, for example, centrifugation, and then optionally washed, and frozen or lyophilized.

In some specific aspects, the inner portion of the microparticles comprise a synthetic biodegradable copolymer, such as poly(lactide-co-glycolide) and an outer portion of the microparticles comprise a synthetic biodegradable homopolymer, such as poly(lactide).

Blends of these polymers with other biodegradable polymers can also be used. Typically, release of a bioactive agent occurs as these polymers dissolve or degrade in situ.

The present invention provides effective methods for the delivery of bioactive agents from a polymeric matrix. The matrix includes at least one set of microparticles, wherein the at least one set of microparticles includes a hydrophilic bioactive agent. The hydrophilic bioactive agent can be released from the microparticles and the polymeric matrix entrapping the microparticles, into an environment (such as fluid or tissue) that is in contact with the matrix.

In some aspects, the matrix with microparticles can be fabricated to release a hydrophilic bioactive agent and one or more other bioactive agents that are different than the hydrophilic bioactive agent. For example, the matrix may include another set of microparticles that include a bioactive agent that has solubility (in water) that is less than the solubility of the hydrophilic bioactive agent. For example, the invention also provides a medical device having a bioactive agent-releasing coating, the coating comprising a matrix of polymeric material comprising a first set of microparticles comprising a first bioactive agent that is hydrophilic, and a second set of microparticles comprising a second bioactive agent that is less soluble in water than the first bioactive agent. The first and second sets of microparticles are immobilized in a polymeric matrix wherein reacted groups allow the polymeric material to be covalently coupled together, to the surface of the device, or both.

The matrix includes a set of microparticles that contain a hydrophilic bioactive agent that has a solubility of at least 1 part agent per 50 parts water. More specifically, and within this embodiment, the hydrophilic bioactive agent may be soluble (having a solubility of at least 1 part agent per from 10 to 30 parts water), freely soluble (having a solubility of at least 1 part agent per from 1 to 10 parts water), or very soluble (having a solubility of greater than 1 part agent per 1 part water). These descriptive terms for solubility are standard terms used in the art (see, for example, *Remington: The Science and Practice of Pharmacy*, 20$^{th}$ ed. (2000), Lippincott Williams & Wilkins, Baltimore Md.).

In some aspects the bioactive agent is an ionizable molecule, referring to compounds that can form ions in an aqueous composition. For example the bioactive agent can be ionizable in an aqueous composition at a physiological pH range (about pH 6-pH 9).

According to the present invention, the hydrophilic bioactive agent is released from the matrix in sustained-release profile, which, as stated, represents an improvement for the delivery of hydrophilic bioactive agents. Given this feature, the matrix with immobilized microparticles can be advantageously used to deliver a hydrophilic bioactive agent alone, or along with one or more other bioactive agents. The one or more other bioactive agents may be more soluble than the hydrophilic bioactive agent, or less soluble than the hydrophilic bioactive agent. For example, in one aspect, the matrix includes at least two sets of microparticles, wherein a first set of microparticles includes a hydrophilic bioactive agent, and a second set of microparticles includes a hydrophobic bioactive agent. Advantageously, the hydrophilic and hydrophobic bioactive agents can be released at a rate to provide an effect within their respective therapeutic windows.

The invention also provides a method for preparing a bioactive agent-releasing coating having a first bioactive agent, and a second bioactive agent that is less soluble in water than the first bioactive agent.

The invention also provides a method for localized, sustained release delivery to a patient of a first bioactive agent, and a second bioactive agent that is less soluble in water than the first bioactive agent. The method comprises a step of placing in a subject a medical device having a coating comprising a polymeric matrix and the first and second sets of microparticles immobilized in the matrix.

The term "bioactive agent," refers to an inorganic or organic molecule, which can be synthetic or natural, that causes a biological effect when administered in vivo to an animal, including but not limited to birds and mammals, including humans.

A partial list of bioactive agents is provided below. One may choose any one of the hydrophilic bioactive agents to be included in a microparticle set alone, or in combination with any other bioactive agent. A comprehensive listing of bioactive agents, in addition to information of the water solubility of the bioactive agents, can be found in *The Merck Index*, Thirteenth Edition, Merck & Co. (2001).

In aspects wherein the matrix comprises first and second sets of microparticles, the first set of microparticles can include a water soluble bioactive agent (such as any water soluble bioactive agent listed herein) and the second set of microparticles can include a bioactive agent that is different than the water soluble bioactive of the first set of microparticles (such as any bioactive agent listed herein).

The matrices prepared according to the invention can be used to release bioactive agents falling within one or more of the following classes include, but are not limited to: ACE inhibitors, actin inhibitors, analgesics, anesthetics, anti-hypertensives, anti polymerases, antisecretory agents, anti-AIDS substances, antibiotics, anti-cancer substances, anticholinergics, anti-coagulants, anti-convulsants, antidepressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

In some aspects the matrix comprises microparticles comprising an antiproliferative agent. The antiproliferative agent can be an anti-angiogenesis agent.

In some aspects the matrix comprises a first set of microparticles comprising an anti-proliferative agent and a second set of microparticles comprising an anti-inflammatory agent.

In some aspects the matrix comprises a first set of microparticles comprising a cell response modifier and a second set of microparticles comprising an anti-inflammatory agent.

In some aspects the matrix comprises a first set of microparticles comprising an antibiotic and a second set of microparticles comprising an anti-inflammatory agent.

In some aspects the matrix comprises a first set of microparticles comprising an anti-thrombotic agent and a second set of microparticles comprising an anti-inflammatory agent.

In some aspects the matrix comprises a first set of microparticles comprising an extracellular matrix protein and a second set of microparticles comprising an immunosuppressive agent.

In some specific aspects, the matrix comprises first and second sets of microparticles, the first set of microparticles comprising a bioactive agent selected from the group consisting of polypeptides, polysaccharides, and polynucleotides and the second set of microparticles comprises a hydrophobic bioactive agent. In some specific aspects the hydrophobic agent comprises a glucocorticoid.

Antibiotics are art recognized and are substances which inhibit the growth of or kill microorganisms. Examples of antibiotics include penicillin, tetracycline, chloramphenicol, minocycline, doxycycline, vancomycin, bacitracin, kanamycin, neomycin, gentamycin, erythromycin, cephalosporins, geldanamycin, and analogs thereof. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Anti-viral agents are substances capable of destroying or suppressing the replication of viruses. Examples of anti-viral agents include α-methyl-P-adamantane methylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine HCl, tacrine, 1-hydroxy-maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl, L(−), deprenyl HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthine, papaverine HCl, indomethacin, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(−), 3-iodotyrosine, alpha-methyltyrosine, L(−) alpha-methyltyrosine, D L(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances that have an anesthetic effect in a localized region. Examples of such anesthetics include procaine, lidocaine, tetracaine and dibucaine.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

Examples of statins include lovastatin, pravastatin, simvastatin, fluvastatin, atorvastatin, cerivastatin, rosuvastatin, and superstatin.

Examples of steroids include glucocorticoids such as cortisone, hydrocortisone, dexamethasone, betamethasone, prednisone, prednisolone, methylprednisolone, triamcinolone, beclomethasone, fludrocortisone, and aldosterone; sex steroids such as testosterone, dihydrotestosterone, estradiol, diethylstilbestrol, progesterone, and progestins.

Exemplary ligands or receptors include antibodies, antigens, avidin, streptavidin, biotin, heparin, type IV collagen, protein A, and protein G.

Exemplary antibiotics include antibiotic peptides.

The bioactive agent can provide antirestenotic effects, such as antiproliferative, anti-platelet, and/or antithrombotic effects. In some embodiments, the bioactive agent can include anti-inflammatory agents, immunosuppressive agents, cell attachment factors, receptors, ligands, growth factors, antibiotics, enzymes, nucleic acids, and the like. Compounds having antiproliferative effects include, for example, actinomycin D, angiopeptin, c-myc antisense, paclitaxel, taxane, and the like.

Representative examples of bioactive agents having antithrombotic effects include heparin, heparin derivatives, sodium heparin, low molecular weight heparin, hirudin, lysine, prostaglandins, argatroban, forskolin, vapiprost, prostacyclin and prostacyclin analogs, D-phe-pro-arg-chloromethylketone (synthetic antithrombin), dipyridamole, glycoprotein Iib/IIIa platelet membrane receptor antibody, coprotein Iib/IIIa platelet membrane receptor antibody, recombinant hirudin, thrombin inhibitor (such as commercially available from Biogen), chondroitin sulfate, modified dextran, albumin, streptokinase, tissue plasminogen activator (TPA), urokinase, nitric oxide inhibitors, and the like.

The bioactive agent can also be an inhibitor of the GPIIb-IIIa platelet receptor complex, which mediates platelet aggregation. GPIIb/IIIa inhibitors can include monoclonal antibody Fab fragment c7E3, also know as abciximab (ReoPro™), and synthetic peptides or peptidomimetics such as eptifibatide (Integrilin™) or tirofiban (Agrastat™).

The bioactive agent can be an immunosuppressive agent, for example, cyclosporine, CD-34 antibody, everolimus, mycophenolic acid, sirolimus, tacrolimus, and the like.

Other exemplary therapeutic antibodies include trastuzumab (Herceptin™), a humanized anti-HER2 monoclonal antibody (moAb); alemtuzumab (Campath™), a humanized anti-CD52 moAb; gemtuzumab (Mylotarg™), a humanized anti-CD33 moAb; rituximab (Rituxan™), a chimeric anti-CD20 moAb; ibritumomab (Zevalin™), a murine moAb conjugated to a beta-emitting radioisotope; tositumomab (Bexxar™), a murine anti-CD20 moAb; edrecolomab (Panorex™), a murine anti-epithelial cell adhesion molecule moAb; cetuximab (Erbitux™), a chimeric anti-EGFR moAb; and bevacizumab (Avastin™), a humanized anti-VEGF moAb.

Additionally, the bioactive agent can be a surface adhesion molecule or cell-cell adhesion molecule. Exemplary cell adhesion molecules or attachment proteins (such as extracellular matrix proteins including fibronectin, laminin, collagen, elastin, vitronectin, tenascin, fibrinogen, thrombospondin, osteopontin, von Willibrand Factor, bone sialoprotein (and active domains thereof), or a hydrophilic polymer such as hyaluronic acid, chitosan or methyl cellulose, and other proteins, carbohydrates, and fatty acids. Exemplary cell-cell adhesion molecules include N-cadherin and P-cadherin and active domains thereof.

Polynucleotides and derivatives thereof include natural and synthetically prepared DNA and RNA polymers, and chemical analogs thereof. Polynucleotides also include oligonucleotides. Exemplary polynucleotides include antisense mRNA, morpholino oligos, siRNA, ribozymes, ssDNA and dsRNA.

This microparticle composition, in conjunction with the polymeric matrix, provides a particularly effective mechanism for the sustained delivery of larger hydrophilic bioactive agents, such as the polypeptides, polysaccharides, or polynucleotides, including any of those previously mentioned, from the matrix. Therefore, in some aspects, the invention provides a medical device having a bioactive agent-releasing coating, the coating comprising a matrix of polymeric material and reacted groups that allow the polymeric material to be covalently coupled together, covalently coupled to the surface of the device, or both. The microparticles immobilized in the matrix comprise a hydrophilic bioactive agent having a molecular weight of 1,000 Da or greater.

Imaging agents may also be included in the microparticle or matrix. These agents are capable of imaging a desired site, e.g., tumor, in vivo. Examples of imaging agents include substances having a label that is detectable in vivo, e.g., antibodies attached to fluorescent labels. The term antibody includes whole antibodies or fragments thereof.

The matrix can be composed of polymeric material (one or more polymers) that allows immobilization of the microparticles. The polymeric material can include one or more homopolymers, copolymers, combinations or blends thereof useful for forming the matrix.

Generally, a polymeric material is chosen and used in a composition suitable for forming a matrix with intact microparticles. For example, a polymer can be chosen which is soluble in a liquid that does not destroy the microparticles. In one desired mode of practice, a hydrophilic polymer is used to prepare an aqueous composition that also includes the microparticles.

Generally, the composition includes an amount and type of polymeric material that provides suitable physical properties (such as durability and microparticle retention). In some aspects the amount of polymeric material used to form the matrix in the composition is at a concentration of about 0.1 mg/mL or greater, 0.5 mg/mL or greater, or 1.0 mg/mL or greater. In one mode of practice the polymeric material is at a concentration of about 2.5 mg/mL.

In aspects where the polymeric material includes pendent photo-reactive or polymerizable groups, the amount of polymer in the composition can also be chosen based on the level of derivitization with these groups.

The amount of microparticles present in the composition can be chosen based on one or more factors, such as the amount of bioactive agent loaded into the microparticles, the rate of release of bioactive agent, and the total amount of bioactive agent to be released from the matrix. The total amount of microparticles can include one set of microparticles for delivery of one bioactive agent, or two or more sets of microparticles for delivery of two or more bioactive agents. The matrix of the present invention is advantageous in that a high loading of microparticles can be achieved. In turn, this facilitates delivery of therapeutically effective amounts of bioactive agent over extended periods of time.

In some aspects microparticles are present in the composition used to form the matrix at a concentration of about 10 mg/mL or greater, 20 mg/mL or greater, 30 mg/mL or greater, or 40 mg/mL or greater. In one mode of practice the microparticles are present in the composition at a concentration of about 50 mg/mL.

If the matrix is formed using two or more sets of microparticles for delivery of two or more types of bioactive agents, the sets of microparticles can be present in any suitable ratio to achieve desired release of the bioactive agents from the matrix.

One class of hydrophilic polymers useful as polymeric materials for matrix formation is synthetic hydrophilic polymers. Synthetic hydrophilic polymers can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these.

Examples of polymers that can be formed from these monomers include poly(acrylamide), poly(methacrylamide), poly(vinylpyrrolidone), poly(acrylic acid), poly(ethylene glycol), poly(vinyl alcohol), and poly(HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,N-dimethylacrylamide-co-aminopropylmethacrylamide) and poly(acrylamide-co-N,N-dimethylaminopropylmethacrylamide) are described in example 2 of Applicants' co-pending U.S. Patent Pub. No. 2006/0030669 filed Sep. 17, 2004 (Taton et al.).

In some embodiments, the hydrophilic polymer is a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Patent Pub. No. 2006/0030669 (Taton et al.).

Natural polymers can also be used to form the matrix. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

Some exemplary natural polymers that can be used to form the matrix are low molecular weight starch-derived polymers as described in commonly assigned U.S. patent application Ser. No. 11/271,213, filed Nov. 11, 2005 (Chudzik et al.). These low molecular weight starch-derived polymers, as exemplified by amylose and maltodextrin, comprise reactive groups, such as polymerizable groups, which can be activated to form a biodegradable matrix that includes microparticles.

In one preferred embodiment, the polymers and copolymers as described are derivatized with a latent reactive group, for example a thermally latent reactive group or a latent photoreactive group. The latent reactive groups can be present at the terminal portions (ends) of the polymeric strand or can be present along the length of the polymer. In one embodiment latent photoreactive groups are located randomly along the length of the polymer. Latent photoreactive groups can be activated to bond to another moiety (such as another polymer, or the surface of a device) to form a reacted group.

Methods of preparing hydrophilic polymers having photoreactive groups are known in the art. For example, methods for the preparation of photo-PVP are described in U.S. Pat. No. 5,414,075.

A latent photoreactive group includes one or more reactive moieties that respond to a specific applied external energy source, such as radiation, to undergo active species generation, for example, active species such as nitrenes, carbenes and excited ketone states, with resultant covalent bonding to an adjacent targeted chemical structure. Examples of such photoreactive groups are described in commonly assigned U.S. Pat. No. 5,002,582 (Guire et al.). Photoreactive groups can be chosen to be responsive to various portions of the electromagnetic spectrum, typically ultraviolet, visible or infrared portions of the spectrum. "Irradiation" refers to the application of electromagnetic radiation to a surface.

Photoreactive aryl ketones are preferred photoreactive groups on the photoreactive polymer, and can be, for example, acetophenone, benzophenone, quinone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone and thioxanthone, and their ring substituted derivatives. Particularly preferred are thioxanthone, and its derivatives, having excitation wavelengths greater than about 360 nm.

The azides are also a suitable class of photoreactive groups on the photoreactive polymer and include arylazides ($C_6R_5N_3$) such as phenyl azide and particularly 4-fluoro-3-nitrophenyl azide, acyl azides (—CO—$N_3$) such as ethyl azidoformate, phenyl azidoformate, sulfonyl azides (—$SO_2$—$N_3$) such as benzensulfonyl azide, and phosphoryl azides $(RO)_2PON_3$ such as diphenyl phosphoryl azide and diethyl phosphoryl azide.

Diazo compounds constitute another suitable class of photoreactive groups on the photoreactive polymers and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as 3-trifluoromethyl-3-phenyldiazirine, and ketenes (—CH=C=O) such as ketene and diphenylketene.

The photoreactive polymer can, in some embodiments, comprise a photoreactive copolymer. The polymer or copolymer can have, for example, a polyacrylamide backbone or be a polyethylene oxide-based polymer or copolymer. One example of a photoreactive polymer comprises a copolymer of vinylpyrrolidone and N-[3-(4-benzoylbenzamido)propyl]methacrylamide (BBA-APMA); another example is a copolymer of acrylamide and BBA-APMA.

The photoreactive groups of the photoreactive polymer can allow the formation of a covalent bond between the substrate and the photoreactive polymer thereby binding the polymer to the surface of the substrate. The photoreactive groups of the photoreactive polymer can also serve to crosslink polymeric strands together, allowing the formation of a network of covalently crosslinked polymeric strands that serve as the matrix in which the microparticles can be entrapped.

In some embodiments, crosslinking compounds, for example photoreactive or thermally activated crosslinkers, can be added to the polymeric material and can be treated to form the matrix. The photoactivatable crosslinking agent can be non-ionic or ionic. The photoactivatable cross-linking agent can include at least two latent photoreactive groups that can become chemically reactive when exposed to an appropriate actinic energy source.

Addition of crosslinking compounds can serve to make the polymeric matrix more durable to use conditions and also can create matrices with smaller pore sizes capable of entrapping smaller microparticles. In forming the polymeric matrix, a mixture including microparticles, the polymer, and a crosslinking compound can be prepared and treated to promote matrix formation. In some cases, the mixture can be applied to a substrate and then treated to form the coating with entrapped microparticles.

One or more appropriate crosslinking compound(s) can be included in a composition that is used to form the matrix with microparticles. A crosslinking compound can be chosen based on the properties of the matrix materials (e.g., one or more polymeric components and the microparticles).

For example, the matrix can be formed using a non-ionic photoactivatable cross-linking agent having the formula $XR_1R_2R_3R_4$, where X is a chemical backbone, and $R_1$, $R_2$, $R_3$, and $R_4$ are radicals that include a latent photoreactive group. Exemplary non-ionic cross-linking agents are described, for example, in U.S. Pat. Nos. 5,414,075 and 5,637,460 (Swan et al., "Restrained Multifunctional Reagent for Surface Modification").

Ionic photoactivatable cross-linking agents can also be used to form the matrix. Some ionic photoactivatable cross-linking agents are compounds having the formula: $X_1$—Y—$X_2$, wherein Y is a radical containing at least one acidic group, basic group, or a salt of an acidic group or basic group. $X_1$ and $X_2$ are each independently a radical containing a latent photoreactive group. For example, a compound of formula I can have a radical Y that contains a sulfonic acid or sulfonate group; $X_1$ and $X_2$ can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments, a non-photoreactive crosslinking agent can be used to promote the formation of crosslinked polymeric strands. A non-photoreactive agent can be added that can be a target for the photoreactive groups, that can initiate further polymerization of the polymers, or that can be a thermochemically activated crosslinker, for example a DSS (N,N-disuccinimidyl suberate) crosslinker.

A coating on the surface of a device can be formed that includes a layer of coated material, the layer of coated material including the matrix of polymeric material and microparticles. The coating can also include one or more additional layers of material. If one or more additional layers are present, these can be the same or different than the layer of coated material including the matrix of polymeric material and microparticles. For example, the coating may include a "base layer" present between the surface of the device and the layer of coated material including the matrix of polymeric material and microparticles. The coating may also include a "top layer" formed on all or a portion of the layer of coated material including the matrix of polymeric material and microparticles.

In one embodiment, a composition including polymeric material and microparticles, which can be coupled to, or associated with, a functional agent, is dip-coated onto the surface of the substrate to form a coated surface. Alternatively, the composition can be applied by jet printing to the surface of the substrate through utilization of a piezoelectric pump. Printing techniques can allow the application of a relatively small amount of the mixture at precise locations on the surface of the substrate. In another embodiment, the composition is disposed on the substrate and treated; the microparticles are then placed and immobilized on the substrate via the treated material.

The coating can be formed on one or more portions of the surface of the substrate. For example, the coating of microparticles can be patterned at various locations on the surface of the substrate. The thickness of the polymeric matrix of each coated portion can vary and can depend on the size of the microparticles immobilized in the polymeric matrix. Preferably, the thickness of the polymeric matrix on the substrate is greater than the diameter of the largest microparticle being disposed on the substrate. In some applications, the substrate can be subject to more than one step of coating with a mixture of polymeric material and microparticles, thereby allowing the formation of multiple layers on the substrate surface.

In order to create a surface coating of immobilized microparticles in a matrix, the mixture, which includes the polymeric material, is typically treated after the mixture is disposed on the substrate. In one embodiment, the polymeric material, which includes a photopolymer, is treated with electromagnetic energy, for example, with UV light, to activate the photoreactive groups of the polymer and to bind the polymer to the substrate or to bind the polymer strands together via crosslinking, or both. In some applications the polymeric material is treated with electromagnetic energy with a mask to form a pattern of treated material on the substrate.

The coatings of the present invention can be provided using a variety of techniques, such as by dip coating, brushing, or spraying. However, a particular spray coating method which disperses the microparticles during the coating process provides a unique and efficient way of providing a microparticle-containing coating to the surface of a medical device. The method can include the steps of (a) agitating a composition comprising the biostable polymeric material and the microparticles comprising a bioactive agent, (b) spray coating the composition on the surface the device, and (c) treating the composition to covalently couple the biostable polymer to the surface. In some cases, the step of agitating is performed in a pressurized chamber, and in some cases the step of agitating and spray coating are performed simultaneously. The method of spray coating can be performed by agitating a composition comprising the biostable polymeric material and the microparticles comprising a bioactive agent, spraying the composition on the surface the device, and then treating the composition to form the coating. In some cases, the step of agitating is performed in a pressurized chamber, and in some cases the step of agitating and spray coating are performed simultaneously. Also spraying can be performed using a pressurized nozzle. In some modes of practice the chamber is pressurized in the range of 0.5-5 psi, and the nozzle is pressurized in the range of 0.5-5 psi. One preferred way of delivering the coating composition is where the chamber has a pressure that is higher than a pressure of the nozzle. Nitrogen can be used as an inert gas to pressurize the chamber.

In one mode of practice, the microparticles are sprayed onto the surface of an implantable medical article in accordance with the methods described in commonly assigned U.S. Provisional Patent Application Ser. No. 60/806,030, filed Jun. 28, 2006 (Slager). Further, a spray coating apparatus and methods as described is U.S. Patent Pub. No. 2004/

0062875 (Chappa et al.) can be used to provide a coating to a surface of an implantable medical device. The spray coating method provides an even coating wherein the microparticles are well dispersed.

Coating compositions including microparticles can be utilized to coat virtually any medical article for which it is desired to provide a functional coating at a surface thereof.

In some cases, a microparticle-containing coating is formed on the surface of a medical article that is introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects, a matrix of polymeric material with microparticles, such as a coating, is utilized in connection with an ophthalmic article. The ophthalmic article can be configured for placement at an external or internal site of the eye. In some aspects, the articles can be utilized to deliver a hydrophilic bioactive agent to an anterior segment of the eye (in front of the lens), and/or a posterior segment of the eye (behind the lens). Suitable ophthalmic devices can also be utilized to provide bioactive agent to tissues in proximity to the eye, when desired. Compositions including polymeric material and microparticles can be used either for the formation of a coating on the surface of an ophthalmic article, or in the construction of an ophthalmic article.

Articles configured for placement at an internal site of the eye can reside within any desired area of the eye. In some aspects, the ophthalmic article can be configured for placement at an intraocular site, such as the vitreous. Illustrative intraocular devices include, but are not limited to, those described in U.S. Pat. No. 6,719,750 B2, which describes a non-linear intraocular device. ("Devices for Intraocular Drug Delivery," Varner et al.) and U.S. Pat. No. 5,466,233 ("Tack for Intraocular Drug Delivery and Method for Inserting and Removing Same," Weiner et al.); U.S. Publication Nos. 2005/0019371 A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), and U.S. application Ser. Nos. 11/204,195 (filed Aug. 15, 2005, Anderson et al.), 11/204,271 (filed Aug. 15, 2005, Anderson et al.), 11/203,981 (filed Aug. 15, 2005, Anderson et al.), 11/203,879 (filed Aug. 15, 2005, Anderson et al.), 11/203,931 (filed Aug. 15, 2005, Anderson et al.); and related applications.

In some cases the medical device is partially or entirely fabricated from a plastic polymer. In this regard, the microparticle-containing coating can be formed on a plastic surface. Plastic polymers include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

Other suitable polymers for the substrate material include polyamides, polyimides, polyolefins, polystyrenes, polyesters, polycarbonates, polyketones, polyureas, acrylonitrile butadiene copolymers, butadiene rubber, chlorinated and chloro-sulfonated polyethylene, polychloroprene, ethylene propylene (EPM) copolymers, ethylene propylene diene (EPDM) copolymers, polyethylene-ethylene propylene diene PE-EPDM copolymers, polypropylene-ethylene propylene diene (PP-EPDM) copolymers, ethylene-vinyl alcohol copolymer (EVOH), polyepichlorihydrin, isobutylene isoprene copolymer, polyisoprene, polysulfides, silicones polymers, nitrile butadiene copolymer/polyvinylchloride blends (NBR/PVC), styrene butadiene copolymers, and vinyl acetate ethylene copolymers, and combinations thereof.

In other cases, the microparticle-containing coating can be formed on a medical device that is partially or entirely fabricated from a metal. Although many devices or articles are constructed from substantially all metal materials, such as alloys, some may be constructed from both non-metal and metal materials, where at least a portion of the surface of the device is metal. The metal surface may also be a thin surface layer. Such surfaces can be formed by any method including sputter coating metal onto all or portions of the surface of the device.

Metals that can be used in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35. These metals, including other alloys or combinations, can be suitable substrates for disposing a coating composition containing microparticles.

The surface of metal-containing medical devices can be pretreated (for example, with a Parylene™-containing coating composition) in order to alter the surface properties of the biomaterial, when desired. Metal surfaces can also be treated with silane reagents, such as hydroxy- or chloro-silanes.

Other surfaces that can be optionally coated include those that include human tissue such as bone, cartilage, skin and teeth; or other organic materials such as wood, cellulose, compressed carbon, and rubber. Other contemplated biomaterials include ceramics including, but not limited to, silicon nitride, silicon carbide, zirconia, and alumina, as well as glass, silica, and sapphire. Combinations of ceramics and metals can also be coated.

While the present methodologies are useful for forming coatings on the surface of medical devices, the compositions of the present invention can also be used to form a polymeric matrix that can be independent of a medical device surface and useful for delivering a hydrophilic bioactive agent in vivo. A polymeric matrix containing microparticles can be formed in situ at a desired site within the body. A composition that includes polymer, reactive groups, and microparticles comprising hydrophilic bioactive agent, as described herein, can be disposed at a location within or on the body and then treated to activate the reactive groups, thereby forming a mass of polymeric material having immobilized microparticles. In some aspects, the matrix preferably includes microparticles comprising a water soluble bioactive agent, a first polymer, and a second polymer, wherein the second polymer modulates the release of the bioactive agent from the matrix. Bioactive agent release from the matrix can restore or improve tissue growth or function by, for example, promoting or permitting formation of new tissue between and into the matrix.

In some aspects, the matrix is formed using a bio-macromer. A bio-macromer refers to a polymerizable, naturally occurring polymer or naturally occurring polymer derivative. A biomacromer can be formed by obtaining a naturally occurring polymer or portion thereof, and derivatizing the polymer to add polymerizable groups, such as ethylenically unsaturated groups. The biomacromer can be formed from a naturally occurring polysaccharide or polypeptide.

After the composition is delivered to a desired site in the body, it can be treated in situ to form a matrix of polymerized material. For example, the treatment may include irradiating the composition with long wave UV or visible light in the presence of a suitable photoinitiator activated by these particular wavelengths. One such exemplary system is described in U.S. Patent Pub. No 2006/0287410 (Chudzik et al.), which describes a water-soluble camphorquinone photoinitiator and a hyaluronic acid macromer. As another example, the treatment may include promoting matrix formation by a redox polymerization system in the presence of a biomacromer and microparticles. One such exemplary system is described in U.S. patent application Ser. No. 11/271,238 (Chudzik et al.; In Vivo Formed Matrices Including Natural Biodegradable Polysaccharides and Uses Thereof; filed Nov. 11, 2005), which describes a peroxide-based redox system and a maltodextrin macromer.

Many polysaccharides and polypeptides are degradable by enzymes present in the body. The matrix can be formed in such a manner to retain the microparticles during release of the bioactive agent. For example, biodegradable microparticles with bioactive agent are preferably degraded at a rate that is faster than the degradation of the biodegradable polymer used to form the polymeric matrix.

According to aspects of the invention, the matrix with microparticles is prepared so the hydrophilic bioactive agent is released from the coating in sustained-release profile. This feature allows for release of the hydrophilic bioactive agent from an implantable medical device over a longer and more therapeutically useful time period.

Release of the bioactive agent (in vitro) can be manually or automatically measured using standard elution techniques. For example, a suitable automated system that can perform elution and detection of bioactive agent from the matrix is a Sotax USP 4 instrument (Sotax Corporation; Horsham, Pa.). Elution of drug from the matrix can be assessed using a solution such as PBS circulating through the closed loop system. Bioactive agent release can be monitored spectrophotometrically at the peak absorbance of the bioactive agent.

The invention provides coatings having specific hydrophilic bioactive agent release profiles. The release profiles allow for sustained release of the hydrophilic bioactive agent over a period of time, avoiding a short burst and premature depletion of the bioactive agent from the matrix.

In some aspects, the coating has a bioactive agent release profile wherein 50% of the hydrophilic bioactive agent present in the coating is released within a period of 1 to 27 days. In some aspects, for example, 50% of the bioactive agent present in the coating can be released on or after a period of 3, 5, or 7 days, but on or before 17, 15, 13, or 11 days. In more specific cases, the 50% of the hydrophilic bioactive agent present in the coating is released within a period of 7 to 11 days.

In other aspects, the hydrophilic bioactive agent has a molecular weight of 1,000 Da or greater, and the coating has a release profile wherein 50% of the bioactive agent present in the coating is released within a period of 1 to 29 days.

In another aspect, the coating includes a matrix of polymeric material with a first set of microparticles comprising a first hydrophilic bioactive agent, and a second set of microparticles comprising a second bioactive agent that is less soluble in water than the first bioactive agent. For example, the first bioactive agent can have a solubility of at least 1 part agent per 50 parts water, and the second bioactive agent can have a solubility of less than 1 part agent per 50 parts water. As another example, the first bioactive agent is soluble in water and the second bioactive agent is practically insoluble or insoluble in water. In yet other specific aspects, the first and second bioactive agents have molecular weights of 400 Da or less.

The coating can have a release profile wherein the first and second bioactive agents are released from the coating at rates wherein not more than 50% either the first or second bioactive agent is released from the coating within a period of 24 hours.

In more specific aspects, 25% of the first bioactive agent and 50% of the second bioactive agent present in the coating are released at time points within a period of 4.7 hours to 8 days.

Release of a bioactive agent from a coating can be initiated by implanting a device having a coating containing microparticles into a subject. Following implantation, the one or more bioactive agents can be released in a sustained profile to provide a therapeutic effect to a subject.

The following examples illustrate the present invention without, however, limiting the same thereto.

EXAMPLES

Example 1

Diclofenac/PLGA Microparticles Immobilized in a Polymer Layer

Degradable microspheres were prepared containing a hydrophilic, water-soluble anti-inflammatory agent and then immobilized on a substrate surface in a polymeric matrix. The microsphere-coated substrate was then placed in media and the release of the anti-inflammatory agent from the surface of the substrate was quantified over a period of time.

Poly(lactide-co-glycolide) (PLGA) microspheres loaded with diclofenac were prepared by an oil-in-water emulsion/solvent evaporation technique (Wichert, B. and Rohdewald, P. (1993) *J. Microencapsul.* 10:195). In a first step, 30 or 100 mg of fine-particulate diclofenac (Aldrich, St. Louis, Mo.) were combined with 100 mg of PLGA (50:50 lactide:glycolide; average MW 50,000-75,000 daltons; Aldrich, St. Louis, Mo.) dissolved in 15 ml of dichloromethane. The mixture was homogenized at Speed 20 using a Tissue Tearor (Biospec Products; Bartlesville, Okla.) for 1.0 minute. The emulsion was poured into 40 ml of 0.3% (w/v) aqueous polyvinyl alcohol (PVA) solution (Aldrich, St. Louis, Mo.) containing 4 g NaCl and then stirred for one hour. The mixture was then centrifuged for 10 minutes. The microspheres were isolated and washed with 20 ml deionized (DI) water twice. The wet microspheres were then lyophilized. To ascertain the diclofenac loading of the microparticles, 12 mg of microparticles were dissolved in 4 ml of 10% NaOH and placed on a shaker in a 55° C. oven for one hour, diluted 10:1 with DI water, and then the absorbance was measured at 276 nm on a Shimadzu spectrophotometer (Model UV-1601, Columbia, Md.). The two sets of microparticles were determined to contain 1.6 and 2.1% (w/w) diclofenac, respectively.

For each set, a slurry of 30 mg diclofenac-PLGA microparticles in 800 µl of 2.5 mg/ml aqueous solution of photoreactive poly(vinylpyrrolidone) copolymer (Photo-PVP), prepared as described in Example 4 of U.S. Pat. No. 5,414,075, was prepared and sonicated to re-suspend the microparticles. For each set, the slurry was cast on approximately half the area of a 1"×3" polystyrene sheet (PS) (Goex Plastics, Janesville, Wis.). The film formed on the polystyrene sheet was allowed to dry for one hour at room temperature followed by irradiation with UV light (Dymax, Light-Welder PC-2, Torrington, Conn.) for three minutes. The coated PS sheets were then tested for drug elution using a Sotax USP 4 instrument (Sotax Corporation; Horsham, Pa.). The elution medium used was PBS, pH 7.4. Elution of drug from the coatings was assessed using a Sotax USP 4 instrument (Sotax Corporation; Horsham, Pa.). Samples were placed in a 12 mm cell, using 35 ml of phosphate buffer solution (PBS) at 37° C. circulating through the closed loop system. The elution experiment with the Sotax system was run for 3 days, monitoring absorbance at 276 nm. The amount of diclofenac released from the two sets of microparticle-coated PS sheets as a function of time is shown in Table 1. The results indicated that the diclofenac was released very fast (within a few hours) from these coatings.

TABLE 1

Percent diclofenac released from coating

| Time (hours) | Sample 1 | Sample 2 | Sample 3 | Sample 4 | Sample 5 | Sample 6 | Average |
|---|---|---|---|---|---|---|---|
| 0 | 0 | 0 | 0 | 0 | 0 | 0 | 0 |
| 0.5 | 51.2 | 52.1 | 49.6 | 46.6 | 51.0 | 68.7 | 53.2 |
| 1 | 77.9 | 78.6 | 75.9 | 70.0 | 80.6 | 90.9 | 79.0 |
| 2 | 98.8 | 98.3 | 97.4 | 93.4 | 99.6 | 99.5 | 97.8 |
| 4 | 100.0 | 99.8 | 99.8 | 99.1 | 100.4 | 99.6 | 99.8 |
| 8 | 100.2 | 99.9 | 100.0 | 99.2 | 100.3 | 99.8 | 99.9 |
| 24 | 100.0 | 107.9 | 100.0 | 99.3 | 100.2 | 99.9 | 101.2 |
| 48 | 100.1 | 100.0 | 100.0 | 99.7 | 100.0 | 99.9 | 99.9 |

Example 2

Diclofenac/PLGA Microparticles Immobilized in a Polymer Layer with an Additional Polymer Topcoat Degradable microspheres were prepared containing a hydrophilic, water-soluble anti-inflammatory agent and then immobilized on a substrate surface in a polymeric matrix. An additional polymer topcoat was added after the microsphere/polymer layer. The microsphere-coated substrate was then placed in media and the release of the anti-inflammatory agent from the surface of the substrate was quantified over a period of time.

Poly(Lactide-co-Glycolide) (PLGA) microspheres Loaded with diclofenac were prepared similar to the method described in Example 1. In a first step, 11 mg of fine-particulate diclofenac (Aldrich, St. Louis, Mo.) was dissolved in 100 ul of acetic acid and 200 ul of dichloromethane. A second solution was prepared containing 110 mg of PLGA (50:50 lactide:glycolide; average MW 50,000-75,000 daltons; Aldrich, St. Louis, Mo.) dissolved in 1.0 ml of dichloromethane. The two solutions were combined and 6 ml of 0.3% (w/v) aqueous polyvinyl alcohol (PVA) solution (Aldrich, St. Louis, Mo.) were added. The mixture was homogenized at speed 18 for 30 seconds using a Tissue Tearor (Biospec Products; Bartlesville, Okla.). The emulsion was poured into 40 ml of 0.03% (w/v) aqueous polyvinyl alcohol (PVA) solution (Aldrich, St. Louis, Mo.) and stirred for three hours. The mixture was then centrifuged and the recovered microspheres were washed with 20 ml DI water three times. The wet microspheres were then lyophilized. The yield of the microspheres was 92%. To ascertain the diclofenac loading, 12 mg of microparticles were dissolved in 4 ml of 10% NaOH and placed on a shaker in a 60° C. oven for two hours, diluted 100:1 with DI water, and then the absorbance was measured at 276 nm on a Shimadzu spectrophotometer (Model UV-1601, Columbia, Md.). The microparticles were determined to contain 6.5% (w/w) diclofenac.

PS sheets (1"×3"; Goex Plastics, Janesville, Wis.) were coated first with a primer layer of Photo-PVP. A first solution of Photo-PVP was dissolved at 2.5 mg/ml in IPA. 100 ul of this solution was pipetted onto each slide and the solution was allowed to dry. The PS sheets were illuminated for 1.0 minute using UV light (Dymax, Light-Welder PC-2, Torrington, Conn.). Next, a slurry of 20 mg diclofenac-PLGA microparticles in 400 ul of 2.5 mg/ml aqueous solution of Photo-PVP was prepared and the pH adjusted to 2-3 with acetic acid. The slurry (100 ul) was cast on approximately half the area of each 1"×3" PS sheet. The film formed on the polystyrene sheet was allowed to dry at room temperature followed by irradiation with UV light (Dymax, Light-Welder PC-2, Torrington, Conn.) for one minute. Then 200 ul of the first solution of Photo-PVP in IPA (2.5 mg/ml) was applied on top of the microsphere-containing layer. The solution was air dried and then illuminated with the same UV system for 2 minutes. The coated sheets were then placed in a desiccator under vacuum overnight.

The coated PS sheets were then tested for drug elution using a Sotax USP 4 instrument. The elution medium used was PBS, pH 7.4. The elution experiment with the Sotax system was run for 3 days. The amount of diclofenac released from the microparticle-coated PS sheets as a function of time is shown in Table 2. As in Example 1, the diclofenac eluted very quickly from these microparticle-containing coatings.

TABLE 2

| Time | Percent diclofenac released from coating | | | |
|---|---|---|---|---|
| (hours) | Sample 1 | Sample 2 | Sample 3 | Average |
| 0 | 0 | 0 | 0 | 0 |
| 0.5 | 38.7 | 37.1 | 39.3 | 38.4 |
| 1 | 40.1 | 38.7 | 41.3 | 40.1 |
| 2 | 42.7 | 41.3 | 44.7 | 42.9 |
| 4 | 46.9 | 45.7 | 49.6 | 47.4 |
| 8 | 53.2 | 53.7 | 56.8 | 54.6 |
| 24 | 75.3 | 77.0 | 77.1 | 76.4 |
| 48 | 91.5 | 92.6 | 92.3 | 92.2 |
| 72 | 98.9 | 99.0 | 98.5 | 98.8 |
| 96 | 100.0 | 99.6 | 99.3 | 99.6 |
| 120 | 101.0 | 100.5 | 100.0 | 100.5 |

Example 3

Double-Walled Diclofenac Microparticles in Polymer Coating

Degradable microspheres having a double-layer of biodegradable polymers were prepared containing a hydrophilic, water-soluble anti-inflammatory agent and then immobilized on a substrate surface in a polymeric matrix. The microsphere-coated substrate was then placed in media and the release of the anti-inflammatory agent from the surface of the substrate was quantified over a period of time.

Poly(lactide-co-glycolide) (PLGA): poly-L-lactide (PLLA) double-walled microspheres loaded with diclofenac were prepared as follows. A solution of PLLA was prepared by dissolving 300 mg of PLLA (Aldrich, St. Louis, Mo.) in 1.0 ml dichloromethane. A second solution was made by dissolving 150 mg PLGA (50:50 lactide:glycolide; average MW 50,000-75,000 daltons; Aldrich, St. Louis, Mo.) in 0.8 ml dichloromethane; 50 mg of fine-particulate diclofenac (Aldrich, St. Louis, Mo.) was then added to the PLGA solution. The two solutions were left to dissolve overnight. The PLGA/diclofenac solution was then sonicated (Misonix, Inc; Farmingdale, N.Y.) and then the PLLA solution was added to the PLGA/diclofenac solution and sonicated for another 30 seconds at power level 3. Next, 8 ml of 1.0% (w/v) aqueous polyvinyl alcohol (PVA) solution (Aldrich, St. Louis, Mo.) was added to the emulsion. The emulsion was vortex mixed for 30 seconds. The mixture was then poured into 200 ml of 0.5% (w/v) PVA in water while stirring. After one hour, the mixture was centrifuged and the recovered microspheres were washed with 30 ml DI water three times. The microspheres were then re-suspended in 10 ml of DI water, frozen at −20° C., and then lyophilized. To ascertain the diclofenac loading, 11.4 mg of microparticles were dissolved in 4 ml of 10% NaOH then 16 ml of DI water was added. After four hours, a sample of the solution was diluted 10:1 with DI water, and then the absorbance was measured at 276 nm on a Shimadzu spectrophotometer (Model UV-1601, Columbia, Md.). The microparticles were determined to contain 5.1% (w/w) diclofenac.

PS coverslips (1.1 cm×2.3 cm; Nunc, Rochester, N.Y.) were coated with a primer layer of Photo-PVP. A first solution of Photo-PVP was dissolved at 2.5 mg/ml in IPA. 100 ul of this solution was pipetted onto each cover slip and the solution was allowed to dry. The PS coverslips were illuminated for 1.0 minute using UV light (Dymax, Light-Welder PC-2, Torrington, Conn.). Next, a slurry was prepared with 5 mg diclofenac-PLGA/PLLA microparticles in 100 ul of 2.5 mg/ml aqueous solution of Photo-PVP. The slurry (100 ul) was cast on the PS coverslip. The film formed on the PS was allowed to dry at room temperature followed by irradiation with UV light (Dymax, Light-Welder PC-2, Torrington, Conn.) for 2.0 minutes. Then 200 ul of the first solution of Photo-PVP in IPA (2.5 mg/ml) was applied on top of the microsphere-containing layer. The solution was air dried and then illuminated with the same UV system for 2 minutes.

The elution of drug from the microparticles in the coatings was assessed by incubating the coated PS coverslips in PBS at 37° C. Three coated coverslips were immersed individually in 30 ml of PBS and placed in a 37° C. incubator. At various times, 1 ml of solution was removed from each vial and 1 ml of fresh PBS was added. The removed solution was assessed for drug content by measuring UV absorbance at 276 nm. The amount of diclofenac released as a function of time is shown in Table 3. The results demonstrate that more sustained release can be achieved with the double-walled compared with the single-walled microparticles, when immobilized in the polymer coating.

TABLE 3

| Time | Percent diclofenac released from coating | | | |
|---|---|---|---|---|
| (hours) | Sample 1 | Sample 2 | Sample 3 | Average |
| 0 | 0 | 0 | 0 | 0 |
| 1 | 1.9 | 2.2 | 1.9 | 2.0 |
| 3 | 2.6 | 3.0 | 2.7 | 2.8 |
| 5 | 3.1 | 3.3 | 3.1 | 3.2 |
| 24 | 7.2 | 8.0 | 7.8 | 7.7 |
| 72 | 12.0 | 12.3 | 11.5 | 11.9 |
| 120 | 23.0 | 22.4 | 20.3 | 21.9 |
| 168 | 40.8 | 38.6 | 36.0 | 38.5 |
| 216 | 55.4 | 53.3 | 51.5 | 53.4 |
| 264 | 72.4 | 68.6 | 68.4 | 69.8 |
| 312 | 81.4 | 77.9 | 76.8 | 78.7 |
| 360 | 89.6 | 87.2 | 86.2 | 87.6 |
| 408 | 94.3 | 92.5 | 91.1 | 92.7 |
| 480 | 93.9 | 93.4 | 91.7 | 93.0 |
| 504 | 94.0 | 93.4 | 92.0 | 93.1 |
| 552 | 93.2 | 92.7 | 91.7 | 92.5 |
| 648 | 94.1 | 94.0 | 92.7 | 93.6 |

In order to demonstrate the effect of the double-walled microparticle coatings on the release rate of diclofenac as compared to the single-walled microparticle coatings, and single walled microparticle coatings having a polymeric topcoat, the data from Tables 1, 2, and 3 was charted and is shown in FIG. 1. The values on the Y-axis represent percentage of diclofenac released from the coating, and the values on the X axis represent time. The 0 time point is the start of the elution.

Example 4

Preparation of Single-Walled and Double-Walled Dexamethasone Microparticles

Two types of dexamethasone-containing microparticles were prepared using a single biodegradable polymer or a double layer of two biodegradable polymers.

Poly(lactide-co-glycolide) (PLGA) single-walled microspheres loaded with dexamethasone were prepared as follows. A solution was made by dissolving 200 mg PLGA (50:50 lactide:glycolide; average MW 50,000-75,000 daltons; Aldrich, St. Louis, Mo.) in 2 ml dichloromethane. 100 mg dexamethasone (Aldrich, St. Louis, Mo.) was added to this solution. The suspension was vortex mixed and then 6 ml of 1.0% (w/v) aqueous polyvinyl alcohol (PVA) solution (Aldrich, St. Louis, Mo.) was added to the solution and the mixture was homogenized at speed 15 for 1 minute using a Tissue Tearor (Biospec Products; Bartlesville, Okla.). The mixture was then poured into 40 ml of 0.3% PVA in water while stirring for 1.5 hours. The mixture was centrifuged and the recovered microspheres were washed with 30 ml DI water three times. The microspheres were then re-suspended in 15 ml of DI water and frozen on a dry ice/acetone bath. Finally, the particles were lyophilized. To ascertain the dexamethasone loading, 11.5 mg of microparticles were dissolved in a solvent mixture of 1 ml of dichloromethane and 3 ml of acetonitrile. Then 10 ul of the solution were added to 990 ul of methanol. The absorbance of this solution was measured at 242 nm on a Shimadzu spectrophotometer (Model UV-1601, Columbia, Md.). The microparticles were determined to contain 28.1% (w/w) dexamethasone Poly(lactide-co-glycolide) (PLGA): poly-L-lactide (PLLA) double-walled microspheres loaded with dexamethasone were prepared as follows. A solution of PLLA was prepared by dissolving 300 mg of PLLA (MW 100,000-150,000 daltons, Aldrich, St. Louis, Mo.) in 1.0 ml dichloromethane. A second solution was made by dissolving 150 mg PLGA (50:50 lactide:glycolide; average MW 50,000-75,000 daltons, Aldrich, St. Louis, Mo.) in 1.0 ml dichloromethane. 225 mg of dexamethasone (Aldrich, St. Louis, Mo.) was added to the PLGA solution. The PLGA/dexamethasone solution was then vortex mixed to make a homogeneous suspension. Then 1.0 ml of the PLLA solution was added to the PLGA/dexamethasone solution and sonicated (Misonix, Farmingdale, N.Y.) for another 30 seconds at power level 3. Next, 8 ml of 1.0% (w/v) aqueous polyvinyl alcohol (PVA) solution (Aldrich, St. Louis, Mo.) was added to the emulsion. The emulsion was homogenized using a Tissue Tearor (Biospec Products; Bartlesville, Okla.) at speed 15 for 1 minute. The mixture was then poured into 200 ml of 0.5% PVA in water and stirred for 1.5 hours. The mixture was centrifuged and the recovered microspheres were washed with 30 ml DI water three times. The microspheres were then re-suspended in 10 ml of DI water and frozen at −20° C. Finally, the particles were lyophilized. To ascertain the dexamethasone loading, 8.8 mg of microparticles were dissolved in a solvent mixture of 4 ml of dichloromethane and 4 ml of acetonitrile. Then 10 ul of the solution were added to 990 ul of methanol. The absorbance of the resulting solution was measured at 242 nm on a Shimadzu spectrophotometer (Model UV-1601, Columbia, Md.). The microparticles were determined to contain 31.5% (w/w) dexamethasone.

Example 5

Preparation of Double-Walled Trigonelline/PLGA/PLLA Microspheres

Degradable microspheres having a double-layer of biodegradable polymers were prepared containing a hydrophilic, water-soluble drug mimic Poly(lactide-co-glycolide) (PLGA): poly-L-lactide (PLLA) double-walled microspheres loaded with trigonelline-HCl were prepared as follows. A solution of PLLA (MW 100,000-150,000 daltons, Aldrich, St. Louis, Mo.) was prepared by dissolving 300 mg of the polymer in 1.0 ml dichloromethane. A second solution was made by dissolving 150 mg PLGA (50:50 lactide:glycolide; average MW 50,000-75,000 daltons, Aldrich, St. Louis, Mo.) in 0.8 ml dichloromethane. 50 mg of fine-particulate trigonelline-HCl (Sigma, St. Louis, Mo.) was added to the PLGA solution. The PLGA/trigonelline solution was then sonicated (Misonix, Farmingdale, N.Y.) at power level 3 and then the PLLA solution was added to the PLGA/trigonelline solution and soni-cated for another 30 seconds at power level 3. Next, 8 ml of 1.0% (w/v) aqueous polyvinyl alcohol (PVA) solution (Aldrich, St. Louis, Mo.) was added to the emulsion. The emulsion was homogenized using a Tissue Tearor (Biospec Products; Bartlesville, Okla.) at speed 15 for 1.0 minute. The mixture was then poured into 200 ml of 0.5% PVA in water while stirring. After one hour, the mixture was centrifuged and the recovered microspheres were washed with 30 ml DI water three times. The microspheres were then re-suspended in 10 ml of DI water and subsequently lyophilized. To ascertain the trigonelline loading, 8.5 mg of microparticles were dissolved in 4 ml of 10% NaOH and incubated at 55° C. for one hour. The solution was diluted 10:1 with DI water, and then the absorbance was measured at 264 nm on a Shimadzu spectrophotometer (Model UV-1601, Columbia, Md.). The microparticles were determined to contain 1.0% (w/w) trigonelline.

Example 6

Release of Two Drugs from Polymer Coatings Containing Diclofenac/PLGA/PLLA and Dexamethasone/PLGA Microspheres In this experiment, coatings were prepared which contained two types of microspheres, single-walled dexamethasone/PLGA microspheres and double-walled diclofenac/PLGA/PLLA microspheres. It was demonstrated that the release of the two drugs from a polymer coating was feasible and the drug release rates were independently determined by the formulation of the microspheres.

Single-walled dexamethasone-PLGA microspheres were prepared and characterized as described in Example 4. Double walled diclofenac-PLGA/PLLA microspheres were prepared and characterized as described in Example 3. PVC coupons (1 cm×2 cm; Fisher Scientific, Hampton, N.H.) were cleaned with IPA and then coated with a primer layer of Photo-PVP. A first solution of Photo-PVP was dissolved at 2.5 mg/ml in IPA. 100 ul of this solution was pipetted onto each coupon and the solution was allowed to dry. The PVC coupons were illuminated for 3 minutes using UV light (Dymax, Light-Welder PC-2, Torrington, Conn.). Next, the PVC coupons were coated with a slurry containing 2.5 mg diclofenac-PLGA/PLLA microparticles and 2.5 mg dexamethasone-PLGA microparticles suspended in 100 ul of a 2.5 mg/ml aqueous solution of Photo-PVP. The film formed on the PVC was allowed to dry at room temperature followed by irradiation with UV light (Dymax, Light-Welder PC-2, Torrington, Conn.) for 1.0 minute. Then 200 ul of the first solution of Photo-PVP in IPA (2.5 mg/ml) was applied on top of the microsphere-containing layer. The solution was air dried and then illuminated with the same UV system for 2 minutes. The coated coupons were dried under vacuum overnight.

The elution of drug from the microparticles in the coatings was assessed by incubating the coated coverslips in PBS, pH 7.4 at 37° C. Three coated coverslips were immersed individually in 30 ml of PBS and placed in a 37° C. incubator. At various times, 1 ml of solution was removed from each vial and 1 ml of fresh PBS was added. The removed solution was assessed for eluted drug content by measuring UV absorbance at 276 nm (diclofenac) and at 242 nm (dexamethasone). The amount of diclofenac and dexamethasone released as a function of time is shown in Table 4.

TABLE 4

| Time (hours) | Percent diclofenac released from coating | Percent dexamethasone released from coating |
| --- | --- | --- |
| 0.17 | 4.9 | 1.8 |
| 0.67 | 8.3 | 3.2 |
| 1.67 | 4.6 | 7.0 |
| 2.67 | 7.0 | 10.2 |
| 4.67 | 4.5 | 15.7 |
| 6.67 | 5.2 | 18.3 |
| 24 | 6.3 | 38.3 |
| 48 | 8.1 | 57.5 |
| 96 | 14.1 | 76.7 |
| 144 | 23.2 | 83.9 |
| 192 | 31.9 | 87.3 |
| 360 | 68.6 | 88.8 |
| 528 | 74.9 | 88.4 |
| 696 | 78.1 | 90.9 |

In order to demonstrate the hydrophilic and hydrophobic drug release profiles of this coating, data from Table 4 was charted and is shown in FIG. 2. The values on the Y axis represent percentage of diclofenac and dexamethasone released from the coating, and the values on the X axis represent time. The 0 time point is the start of the elution. Data from Table 1 was also included to compare the release against a coating including diclofenac without the presence of a second polymer.

Example 7

Elution of DNA from Microspheres in a Polymer Coating

In this experiment, DNA was encapsulated in PLGA microspheres and then the particles were entrapped in a polymer coating. The DNA was demonstrated to elute in a controlled manner from the microparticle-containing coating.

DNA-containing microspheres were prepared by emulsifying 100 ul of herring sperm DNA A solution (Sigma, St. Louis, Mo.) with a solution of 100 mg PLGA in 1.0 ml dichloromethane. Emulsification was accomplished with a probe-type sonicator (Misonix, Farmingdale, N.Y.) run at power level 3 for 15 seconds. Next, 4.0 ml of 1% (w/v) aqueous PVA solution (Aldrich, St. Louis, Mo.) was added. The mixture was homogenized with a Tissue Tearor (Biospec Products; Bartlesville, Okla.) for 1 minute at speed 15. The resultant double emulsion was poured into 40 ml of 0.3% (w/v) PVA while stirring. After 2 hours, the microspheres were collected by centrifugation for 7 minutes. The microspheres were washed with DI water three times and then frozen at −20° C. prior to lyophilization.

PVC cover slips (1 cm×2 cm; Fisher Scientific, Hampton, N.H.) were coated with a primer layer of Photo-PVP. A first solution of Photo-PVP was dissolved at 2.5 mg/ml in IPA. 100 ul of this solution was pipetted onto each cover slip and the solution was allowed to dry. The PS coverslips were illuminated for 3 minutes using UV light (Dymax, Light-Welder PC-2, Torrington, Conn.). Next, a slurry was prepared with 5 mg DNA-PLGA microparticles in 100 ul of 2.5 mg/ml aqueous solution of Photo-PVP. The slurry (100 ul) was cast on the PVC coverslip. The film formed on the PS was allowed to dry at room temperature for 3 hours followed by irradiation with UV light (Dymax, Light-Welder PC-2, Torrington, Conn.) for 1.0 minute. Then 200 ul of the first solution of Photo-PVP in IPA (2.5 mg/ml) was applied on top of the microsphere-containing layer. The solution was air dried and then illuminated with the same UV system for 2 minutes.

The elution of DNA from the microparticles in the coating was assessed by incubating the coated PVC cover slips in PBS, pH 7.4 at 37° C. Three coated coverslips were immersed individually in 10 ml of PBS and placed in a 37° C. incubator. At various times, 1 ml of solution was removed from each vial and 1 ml of fresh PBS was added. The removed solution was assessed for eluted drug content by measuring UV absorbance at 260 nm. The amount of DNA released as a function of time is shown in Table 5.

TABLE 5

| Time (hours) | Percent DNA released from coating |
| --- | --- |
| 0.17 | 0.8 |
| 0.5 | 7.3 |
| 1 | 7.7 |
| 2 | 10.0 |
| 3 | 11.0 |
| 5 | 12.7 |
| 7 | 13.9 |
| 24 | 21.1 |
| 48 | 28.8 |
| 72 | 39.9 |
| 96 | 44.7 |
| 192 | 56.3 |
| 264 | 63.9 |
| 360 | 69.7 |
| 432 | 74.1 |
| 528 | 79.6 |
| 600 | 83.2 |
| 696 | 85.7 |

Example 8

Dip Coating with Dexamethasone-PLGA Microparticles

Dip coating methods were used to prepare microparticle-containing coatings on the surfaces of cylindrical substrate materials.

Dexamethasone-PLGA microspheres (single-walled) were prepared as described in Example 4. PEBAX rods (Medical Profiles, Livonia, Mich.) cut to 2.5 cm length were first coated with a layer of modified Photo-PVP. The Photo-PVP was made by the procedure as previously described. Following the step of photo-derivatization, the unreacted amines of the Photo-PVP were further acetylated using acetic anhydride to give acetylated modified Photo-PVP. The modified Photo-PVP and photo-activatable crosslinker tetrakis(4-benzoylphenylmethoxymethylmethane), prepared as described in Example 1 of U.S. Pat. No. 5,414,075) were dissolved at 15 mg/ml and 0.5 mg/ml respectively in isopropanol (IPA). The rods were dipped into the coating solution allowed to dwell for 1 second and then withdrawn at 0.3 cm/sec. Parts were dried for 10 minutes and then illuminated for 2 minutes using an ultraviolet lamp (Light Welder PC-2, Dymax, Torrington, Conn.). Next, 56 mg of the dexamethasone-PLGA micropheres were added to 15 ml of the modified Photo-PVP solution. In the resulting suspension approximately 20% of the dissolved solids were microspheres. The suspension was rapidly stirred and the PEBAX rods were dip coated using the same application and drying parameters described above. The parts were illuminated for 2 minutes with the same Dymax lamp modified with a 320 nm cut-off filter (ESCO Products, Oak Ridge, N.J.) to reduce the potential for UV light modification of the encapsulated drug or the PLGA polymer.

A second coating procedure was used with another set of PEBAX rods. Modified Photo-PVP and another photoactivatable-crosslinker 4,5-bis(4-benzoylphenylmethyleneoxy)benzene-1,3-disulfonic acid, prepared as described in Example 1 of U.S. Pat. No. 6,278,018, were dissolved in DI water at concentrations of 50 and 1.5 mg/ml, respectively. A total of 150 mg of dexamethasone-PLGA microspheres were added to 5 ml of the modified Photo-PVP/photoactivatable crosslinker solution, creating a solution with 37% of the dissolved solids being microparticles (i.e., 61% modified Photo-PVP polymer and 2% photo-activatable crosslinker). Five PEBAX rods were dip coated using the same coating and drying and illumination parameters as described above for the rods. Three coats were applied to each rod. The total coating weights were measured to determine the amount of coating applied and bonded to the surface. Elution of dexamethasone from the rods was tested using the Sotax USP 4 instrument.

Example 9

Spray Coating with Dexamethasone-PLGA Microspheres in PVP Films

Spray techniques were used to deposit polymer coatings containing microspheres on the surface of PEBAX rods.

PEBAX rods were first base-coated via a dipping process with a modified Photo-PVP coating similar to that described in Example 8. A first solution of modified Photo-PVP was prepared at 20 mg/ml in IPA and applied to the surface of the rods using the dipping, drying, and illumination parameters as in Example 8. The rods were weighed to determine the baseline weight prior to application of the microsphere/polymer layer. Modified Photo-PVP was dissolved in water at a concentration of 10 mg/ml. 40 mg of single-walled dexamethasone-PLGA particles (as prepared in Example 4) were added to 4 ml of the modified Photo-PVP solution. The suspension was loaded into the spray coating apparatus, consisting of a syringe pump connected to an IVEK gas atomization spray system (Digispense™ 2000 Model #4065, IVEK, North Springfield, Vt.). The PEBAX rods were coated along their length with the microparticle/modified Photo-PVP solution and illuminated during the process with an ultraviolet illumination system (EFOS Ultracure 100ss, EXFO UV Curing Systems, Mississauga, Ontario). The weight of the coating applied was determined to estimate the mass of microparticles contained in the coating. This method resulted in the immobilization of microparticle weights ranging from 1,200-1,600 ug in the modified Photo-PVP film on the PEBAX rods. Elution of dexamethasone was tested using the Sotax USP 4 instrument.

What is claimed is:

1. A matrix which releases bioactive agent at a target location in the body where it is implanted or formed in situ, wherein the matrix is formed of a polymeric material that allows fluid to penetrate the matrix, and the matrix comprises at least one set of microparticles immobilized in the matrix, said microparticles comprising, 1) a water-soluble bioactive agent, 2) a first polymer, and 3) a second polymer, wherein one or both first and second polymers are hydrophobic being not soluble in water, and wherein one or both first and second polymers comprise a polysaccharide derivatized with hydrophobic moieties, wherein the second polymer modulates release of the bioactive agent from the matrix as compared to release of the bioactive agent from a matrix comprising microparticles that do not include the second polymer.

2. The matrix of claim 1 wherein the water-soluble bioactive agent comprises an ionizable molecule.

3. The matrix of claim 1 wherein the water-soluble bioactive agent has a molecular weight of less than 1000 Da.

4. The matrix of claim 1 wherein the water-soluble bioactive agent is selected from the group consisting of polypeptides, polysaccharides, and polynucleotides.

5. The matrix of claim 1 wherein the polymeric material comprises reacted groups that covalently couple the polymeric material together, covalently couple the polymeric material to a surface of a device, or both.

6. The matrix of claim 5 wherein the reacted groups comprise photoreactive groups.

7. The matrix of claim 1 wherein the polymeric material comprises a polymer that is more biostable than the first or second polymers of the microparticle.

8. The matrix of claim 1 wherein the polymeric material comprises a synthetic hydrophilic polymer.

9. The matrix of claim 8 wherein the synthetic hydrophilic polymer comprises hydroxyethyl methacrylate, hydroxyethyl acrylate, methacrylic acid, acrylic acid, glycerol acrylate, glycerol methacrylate, acrylamide, methacrylamide, dimethylacrylamide (DMA), vinyl acetate, vinylpyrrolidone, vinyl alcohol, ethylene oxide, propylene oxide, butylene oxide, or combinations thereof.

10. The matrix of claim 1 wherein the first and second polymer include the same type of monomeric residue.

11. The matrix of claim 1 wherein the second polymer comprises a biodegradable homopolymer.

12. The matrix of claim 1 wherein the microparticles comprise an inner core comprising the bioactive agent and the first polymer, and an outer shell comprising the second polymer.

13. The matrix of claim 1 wherein the microparticles have a size of 50 μm or less.

14. The matrix of claim 1 which is in the form of a in situ-formed hydrogel.

15. The matrix of claim 1 which is in the form of a coating on the surface of an implantable medical device.

16. The matrix of claim 1 which is in the form of a coating on the surface of an implantable ocular device.

17. The matrix of claim 1 wherein the water-soluble bioactive agent has a molecular weight of more than 1,000 Da.

18. The matrix of claim 1 wherein the water-soluble bioactive agent is an antibody.

19. The matrix of claim 1 wherein the first and/or second polymer comprises a polysaccharide selected from the group consisting of maltodextrin, amylose, and polyalditol that is derivatized with hydrophobic moieties.

20. The matrix of claim 1, wherein the hydrophobic moieties are selected from $C_2$-$C_{18}$ linear, branched, or cyclic alkyl groups.

21. The matrix of claim 20, wherein the hydrophobic moieties are selected from $C_2$-$C_{10}$ linear, branched, or cyclic alkyl groups.

22. The matrix of claim 21, wherein the hydrophobic moieties are selected from $C_2$-$C_6$ linear, branched, or cyclic alkyl groups.

23. The matrix of claim 1 wherein the polysaccharide is derivatized with hydrophobic moieties at a degree of substitution of greater than 1.

24. A matrix which releases bioactive agent at a target location in the body where it is implanted or formed in situ, wherein the matrix is formed of a polymeric material that allows fluid to penetrate the matrix, and the matrix comprises at least one set of microparticles immobilized in the matrix, said microparticles comprising, 1) a water-soluble bioactive agent, 2) a first polymer, and 3) a second polymer, wherein first and second polymers are hydrophobic being not soluble in water, and said first and second polymers comprise a polysaccharide selected from the group consisting of maltodextrin, amylose, and polyalditol derivatized with hydrophobic moieties at a degree of substitution of greater than 1, wherein the hydrophobic moieties are selected from $C_2$-$C_{18}$ linear, branched, or cyclic alkyl groups, and wherein the second polymer modulates release of the bioactive agent from the matrix as compared to release of the bioactive agent from a matrix comprising microparticles that do not include the second polymer.

* * * * *